(12) United States Patent
Katkam et al.

(10) Patent No.: US 8,779,161 B2
(45) Date of Patent: Jul. 15, 2014

(54) ASENAPINE MALEATE

(75) Inventors: Srinivas Katkam, Hyderabad (IN);
Srinivas Polavarapu, Hyderabad (IN);
Venkata Madhavi Yaddanapudi, Hyderabad (IN); Krishna Vinigari, Hyderabad (IN); Narasimha Rao Pagadala, Hyderabad (IN); Rajeshwar Reddy Sagyam, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 13/703,555

(22) PCT Filed: Jun. 16, 2011

(86) PCT No.: PCT/US2011/040710
§ 371 (c)(1),
(2), (4) Date: Feb. 28, 2013

(87) PCT Pub. No.: WO2011/159903
PCT Pub. Date: Dec. 22, 2011

(65) Prior Publication Data
US 2013/0211099 A1    Aug. 15, 2013

Related U.S. Application Data

(60) Provisional application No. 61/372,566, filed on Aug. 11, 2010, provisional application No. 61/427,933, filed on Dec. 29, 2010.

(30) Foreign Application Priority Data

Jun. 18, 2010  (IN) .......................... 1695/CHE/2010
Nov. 11, 2010  (IN) .......................... 3386/CHE/2010

(51) Int. Cl.
*C07D 491/044*    (2006.01)

(52) U.S. Cl.
USPC ....................................... 548/421

(58) Field of Classification Search
USPC ........................................................ 548/421
See application file for complete search history.

(56) References Cited

U.S. PATENT DOCUMENTS

| 4,145,434 A | 3/1979 | Van Der Burg |
| 5,763,476 A | 6/1998 | Delbressine et al. |
| 2006/0229352 A1 | 10/2006 | Kemperman et al. |
| 2007/0027134 A1 | 2/2007 | Heeres |
| 2008/0090892 A1 | 4/2008 | Casteel et al. |
| 2008/0306133 A1 | 12/2008 | van der Sterren et al. |

FOREIGN PATENT DOCUMENTS

| WO | 99/32018 A1 | 7/1999 |
| WO | 2006/106135 A1 | 10/2006 |

OTHER PUBLICATIONS

International Search Report dated, Mar. 28, 2012 for corresponding International Patent Application No. PCT/US2011/040710.

*Primary Examiner* — Shawquia Young
(74) *Attorney, Agent, or Firm* — Pergament Gilman & Cepeda LLP; Milagros A. Cepeda; Edward D. Pergament

(57) ABSTRACT

Aspects of the present application relate to a microcrystalline monoclinic form of asenapine maleate represented by structural Formula (I); processes for its preparation; and pharmaceutically acceptable dosage forms thereof.

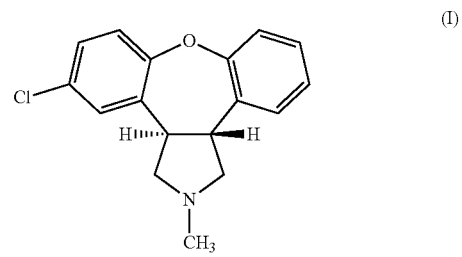

(I)

21 Claims, 4 Drawing Sheets

ASENAPINE MALEATE

This application is a National Stage Application under 35 U.S.C. 371 of PCT International Application No. PCT/US2011/040710, filed Jun. 16, 2011, which claims priority to Indian Provisional Applications 1695/CHE/2010 filed on Jun. 18, 2010; 3386/CHE/2010, filed on Nov. 11, 2010 and U.S. Provisional Applications Nos. 61/372,566 filed on Aug. 11, 2010; 61/427,933 filed on Dec. 29, 2010; all of which are hereby incorporated by reference in their entirety.

Aspects of the present application relate to processes for preparing asenapine and pharmaceutically acceptable salts thereof. Aspects of the present application also relate to a monoclinic form of asenapine maleate, which is stable to micronization; processes for its preparation; and pharmaceutically acceptable dosage forms thereof.

The drug compound having the adopted name "asenapine" has chemical names: trans-5-chloro-2-methyl-2,3,3a,12b-tetrahydro-1H-dibenz[2,3:6,7]oxepino[4,5-c]pyrrole; or (3aRS,12bRS)-5-chloro-2-methyl-2,3,3a,12b-tetrahydro-1H-dibenzo[2,3:6,7]oxepino[4,5-c]pyrrole; and is represented by structural Formula I.

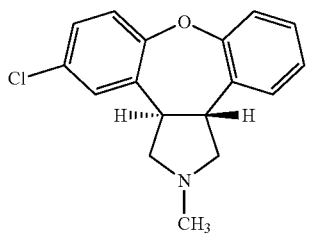

I

The compound corresponding to Formula (I) is a trans-racemate. Both enantiomers within this racemate contribute to the physiologic effects of asenapine. Asenapine maleate, represented by Formula (II), is very potent dopamine and serotonin antagonist with antipsychotic activity, having CNS-depressant activity (Th. de Boer et al., "Org-5222. Antipsychotic, Dopamine $D_2$ Receptor Antagonist, 5-$HT_2$ Receptor Antagonist," Drugs of the Future, 18(12), pp. 1117-1123, 1993) and may be used in the treatment of depression (International Application Publication No. WO 99/32108 A1.

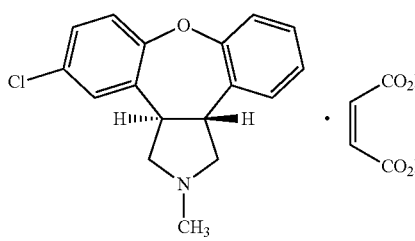

II

Asenapine maleate is the active ingredient in sublingual tablets sold as SAPHRIS®, prescribed for acute treatment of schizophrenia in adults and acute treatment of manic or mixed episodes associated with bipolar I disorder in adults. In pharmaceutical compositions, particularly intended for sublingual and buccal administration, the asenapine is advantageously used as the maleate salt (U.S. Pat. No. 5,763,476).

A methodology, derivable from the teaching of U.S. Pat. No. 4,145,434 and disclosed in full in Example 9 of U.S. Patent Application Publication No. 2006/0229352 A1, for the preparation of asenapine is shown in Scheme 1.

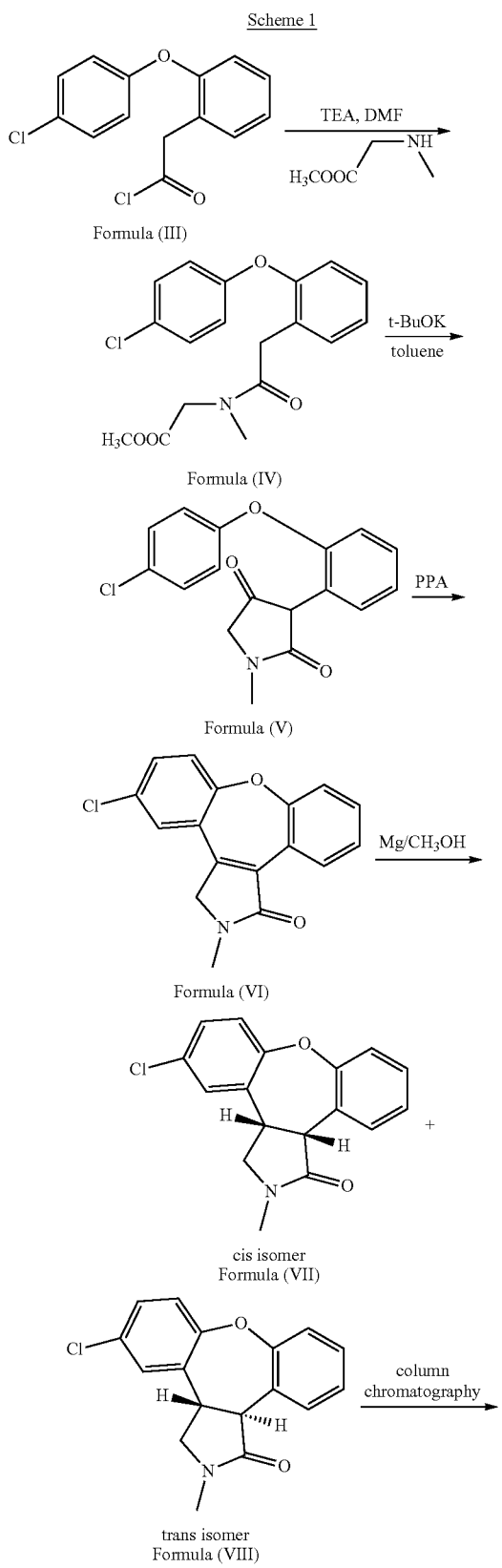

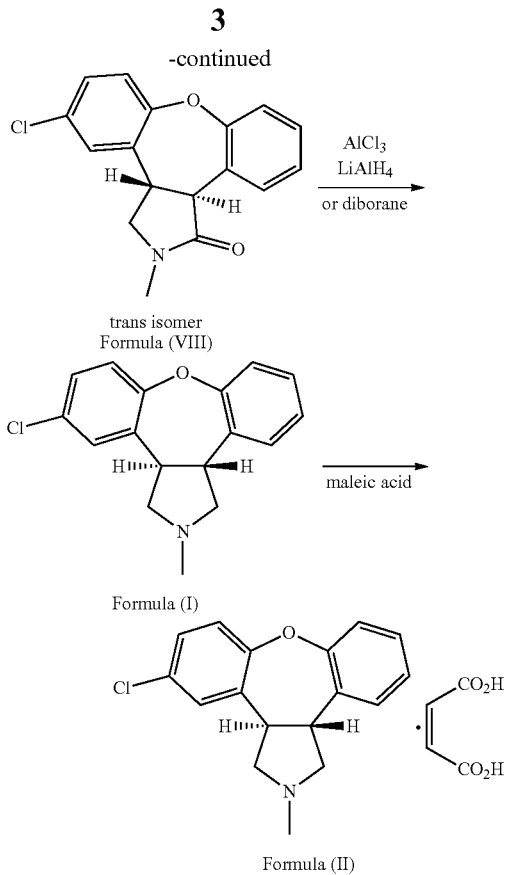

Formula (II)

It appears from the disclosure of US 2006/0229352 A1 that this reaction predominantly provides the unwanted cis-isomer of the compound of Formula VII upon subsequent work up (page 1, para [0006]). The unfavorable product ratio may be improved by subsequent partial isomerization of the unwanted cis-isomer of the Formula VII into the trans-isomer having Formula VIII using 1,5-diazabicyclo[4,3,0]non-5-ene (DBN), yielding a trans-cis equilibrium in approximately a 1:2 ratio. Repeated isomerization may provide an overall 38% yield of the trans-isomer of the Formula VIII, starting from the enamide of Formula VI.

Additional synthetic methods for the preparation of asenapine and radio labeled derivatives thereof have also been described in Vader et al., *Journal of Labeled Compounds and Radiopharmaceuticals*, 34, 845-869, 1994. C. W. Funke et al., "Physico-chemical Properties and Stability of trans-5-Chloro-2-methyl-2,3,3a,12b-tetrahydro-1H-dibenz[2,3:6,7] oxepino[4,5-c]pyrrolidine maleate," *Arzneimittel-Forschung*, 40(5), pp. 536-539, 1990, described physico-chemical properties of a monoclinic form of asenapine maleate having a melting point of 141-145° C.

International Application Publication No. WO 2006/106135 A1 discloses a polymorphic form of asenapine maleate, which is an orthorhombic crystalline form (called "form L") having a melting point in the range of 138-142° C. X-ray diffraction patterns are given for form L and the monoclinic form of Funke et al. (called "form H"). The publication states that a pharmaceutical composition comprising asenapine maleate for sublingual or buccal administration is described in U.S. Pat. No. 5,763,476. For the development of a sublingual formulation, a drug substance with small particle sizes is desired. Smaller particles of drug substance can be achieved by micronization. The outcome of the micronization process, however, appeared to be very unpredictable when crystals of the monoclinic form were subjected to such a process. Analyses of the crystals following micronization revealed the presence of a second polymorph (orthorhombic form L) in addition to the monoclinic form in the starting material. Either the monoclinic form, or the orthorhombic form or a mixture of polymorphs was obtained after micronization starting with the monoclinic form. Even when the starting material was taken from the same batch of the monoclinic form of asenapine maleate, micronization resulted in product that was not reproducible (see Examples 9 and 10 therein). In addition, drug substance with high polymorphic purity could not be obtained by micronization of the monoclinic form of asenapine maleate.

There remains a need to provide improved processes for preparing asenapine and pharmaceutically acceptable salts thereof, which are simple, cost-effective, commercially viable, sustainable, eco friendly and avoid multiple steps. There remains a need for preparing stable and polymorphically pure forms of asenapine maleate.

SUMMARY

Aspects of the present application relate to a monoclinic form of asenapine maleate, which is stable to micronization, and processes for preparation thereof.

In one aspect, the present application provides a monoclinic form of asenapine maleate, which is stable to micronization, with one or more of a powder X-ray diffraction (PXRD) pattern, a differential scanning calorimetry (DSC) curve, and a thermogravimetric analysis (TGA) curve, substantially as illustrated by FIGS. 1, 3, and 4, respectively.

In one aspect, the present application relates to a microcrystalline monoclinic form of asenapine maleate and processes for preparation thereof.

DETAILED DESCRIPTION

Aspects of the present application relate to a monoclinic form of asenapine maleate, which is stable to micronization, and processes for preparation thereof.

In an aspect, the present application provide a monoclinic form of asenapine maleate, which is stable to micronization, with a powder X-ray diffraction (PXRD) pattern having at least two peaks located at about 9.5, 20.3, 21.9, 23.3, 25.1, 26.1, 26.6, 29.0, or 29.9±0.2 degrees 2-theta.

In an aspect, the present application provide a monoclinic form of asenapine maleate, which is stable to micronization, with a powder X-ray diffraction (PXRD) pattern having at least three peaks located at about 9.5, 20.3, 21.9, 23.3, 25.1, 26.1, 26.6, 29.0, or 29.9±0.2 degrees 2-theta.

Figure 1:
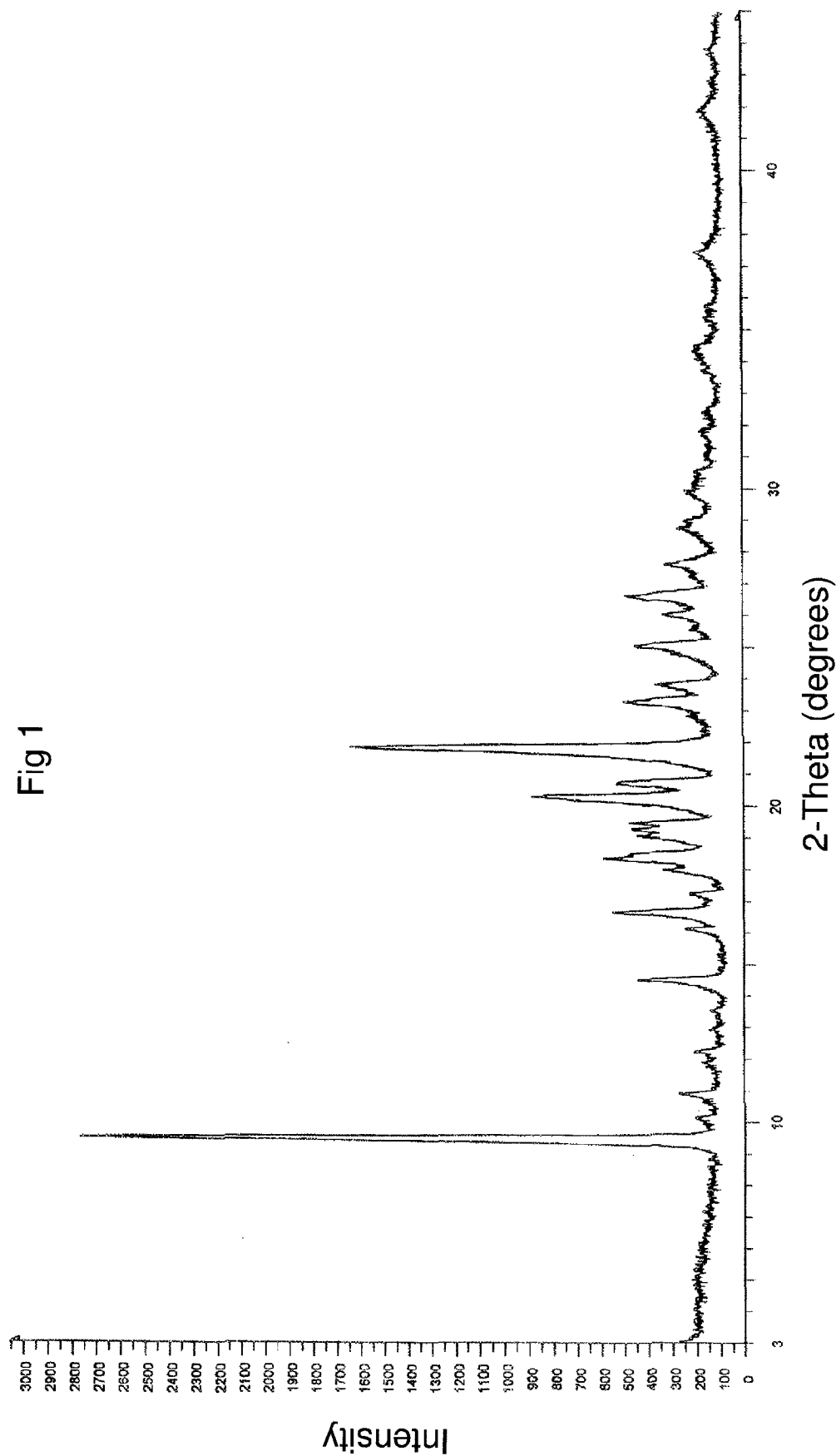
FIG. 1 is an illustration of a PXRD pattern of a monoclinic form of asenapine maleate, which is stable to micronization, prepared according to Example 11.
Figure 3:
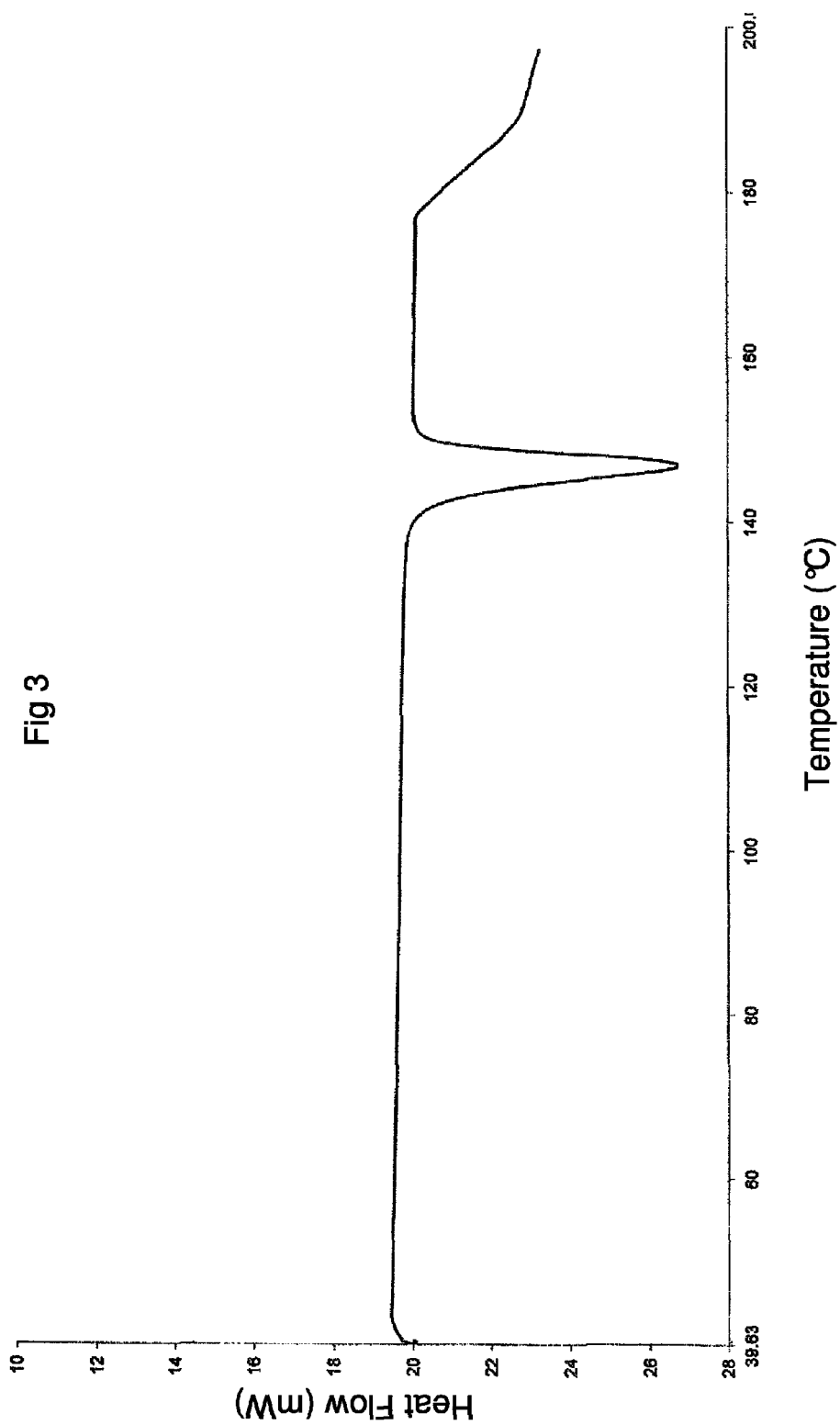
FIG. 3 is an illustration of a DSC curve of a monoclinic form of asenapine maleate, which is stable to micronization, prepared according to Example 11.
Figure 4:
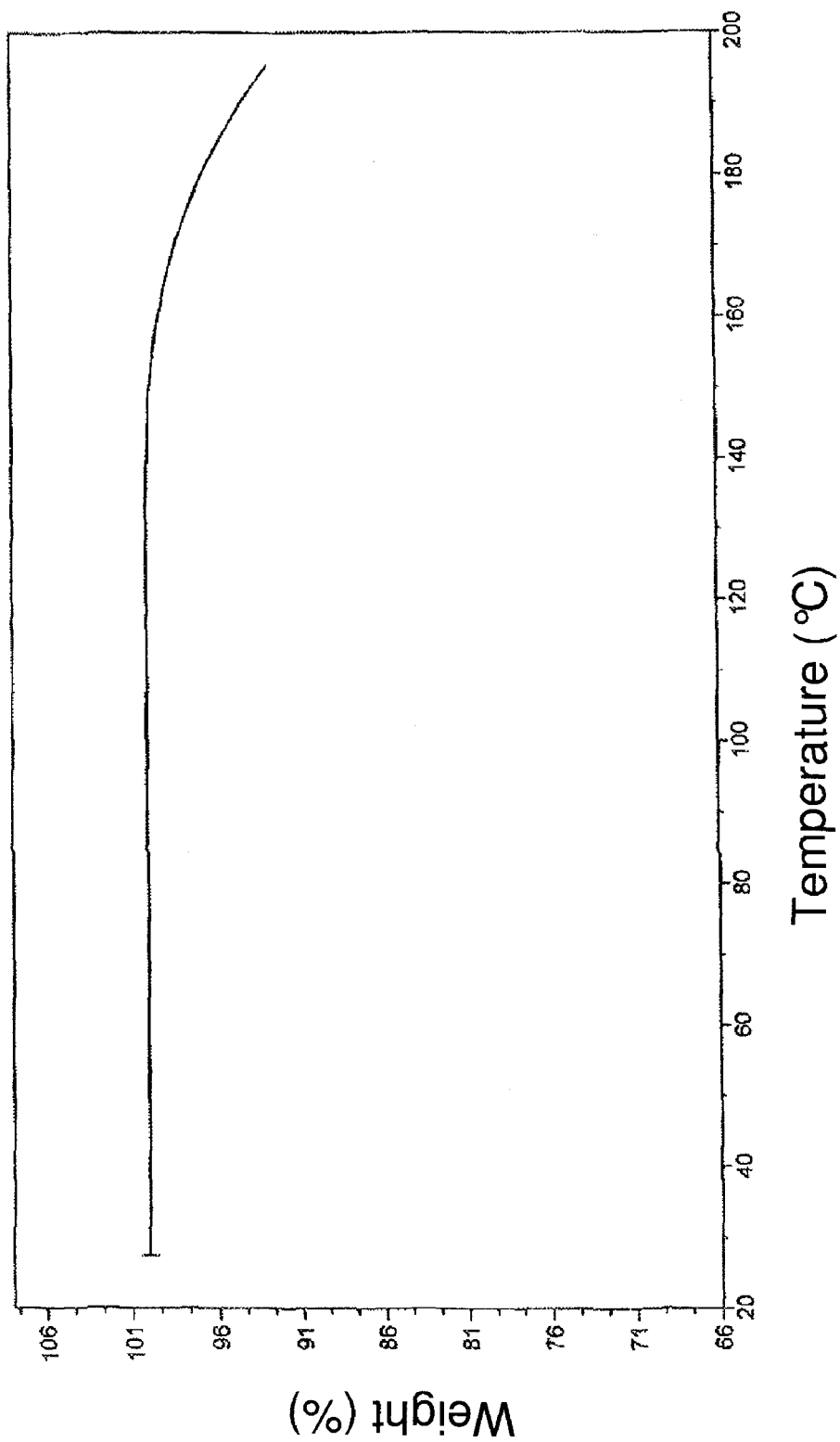
FIG. 4 is an illustration of a TGA curve of a monoclinic form of asenapine maleate, which is stable to micronization, prepared according to Example 11.

In an aspect, the present application provides a monoclinic form of asenapine maleate, which is stable to micronization, with any one or more of a powder X-ray diffraction (PXRD) pattern, a differential scanning calorimetry (DSC) curve, and a thermogravimetric analysis (TGA) curve, substantially as illustrated by FIGS. 1, 3, and 4, respectively.

In an aspect, the present application provides processes for the preparation of a monoclinic form of asenapine maleate, which is stable to micronization, comprising:

a) providing a solution of asenapine in a solvent;

b) combining the solution of asenapine prepared in step a) with a solution of maleic acid in a solvent; and c) isolating the monoclinic form of asenapine maleate.

Step a) involves providing a solution of asenapine in a solvent. The solution of asenapine may be obtained by dissolving asenapine in a solvent, or it may be obtained directly from a reaction mixture, in which the compound is formed in the course of synthesis of asenapine. Any physical forms of asenapine, such as crystalline, amorphous, or their mixtures may be utilized for preparing the solution of asenapine in step a).

Solvents that may be employed for providing a solution of asenapine in step a) include, but are not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof. The temperatures at which a solution may be obtained in step a) range from about 0° C. to about the reflux temperature of the solvent that is used, or any other suitable temperatures.

Step b) involves combining the solution of asenapine obtained in step a) with a solution of maleic acid in a solvent. Alternatively, step b) may be conducted by adding a solution of asenapine to a solution of maleic acid, or adding solution of maleic acid to a solution of asenapine.

Suitable solvents that may be used in step b) include, but are not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof. Suitable temperatures that may be used in step (b) may be less than about 100° C., less than about 80° C., less than about 60° C., less than about 40° C., less than about 30° C., less than about 20° C., less than about 10° C., or any other suitable temperatures.

Step c) involves isolating the monoclinic form of asenapine maleate. Isolation in step c) may involve one or more methods, including removal of solvent, cooling, concentrating the mass, using an anti-solvent, extraction with a solvent, adding seed crystals to induce crystallization, or the like. Stirring or other alternate methods such as shaking, agitation, or the like, may also be employed for the isolation. Suitable temperatures for isolation may be less than about 60° C., less than about 40° C., less than about 20° C., less than about 10° C., less than about 5° C., less than about 0° C., less than about −10° C., less than about −20° C., or any other suitable temperatures. The isolated solid may be recovered by any methods, including decantation, centrifugation, gravity filtration, suction filtration, or any other suitable techniques for the recovery of solids.

The isolated compound may be further purified by recrystallization one or more times from a suitable solvent or a mixture of solvents, such as, but not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof; optionally involving the addition of seed crystals of the monoclinic form. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the asenapine maleate is not degraded in quality. The drying may be carried out for any desired times until the desired product quality is achieved.

The dried product may be subjected to a size reduction procedure to produce desired particle sizes. Milling or micronization may be performed before drying, or after the completion of drying of the product. Techniques that may be used for particle size reduction include, without limitation, ball, roller and hammer milling, or jet milling.

Aspects of the present application relate to a microcrystalline monoclinic form of asenapine maleate and processes for preparation thereof.

In an aspect, the present application provides processes for the preparation of a monoclinic form of asenapine maleate, which is stable to micronization, comprising:

a) providing a solution of asenapine maleate in a solvent;

b) optionally, seeding the solution prepared in step a with crystals of the monoclinic form; and c) isolating the monoclinic form of asenapine maleate.

Step a) involves providing a solution of asenapine maleate in a solvent. The solution of asenapine maleate may be obtained by dissolving asenapine maleate in a solvent, or it may be obtained directly from a reaction mixture, in which the compound is formed in the course of synthesis of asenapine maleate. Any physical forms of asenapine maleate, such as crystalline, amorphous, or their mixtures may be utilized for preparing the solution of asenapine maleate in step a).

Solvents that may be employed for providing a solution of asenapine maleate in step a) include, but are not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof. The temperatures at which a solution may be obtained in step a) range from about 0° C. to about the reflux temperature of the solvent that is used, or any other suitable temperatures.

Step b) involves optionally seeding the solution obtained in step a) with crystals of the monoclinic form. Crystals of monoclinic form that are used in step b) may be obtained by any of the processes of the present application.

Step c) involves isolating the monoclinic form of asenapine maleate. Isolation in step c) may involve any methods, including removal of solvent, cooling, concentrating the mass, using an anti-solvent, extraction with a solvent, adding seed crystals to induce crystallization, or the like. Stirring or other alternate methods such as shaking, agitation, or the like, may also be employed for the isolation. Suitable temperatures for isolation may be less than about 60° C., less than about 40° C., less than about 20° C., less than about 10° C., less than about 5° C., less than about 0° C., or any other suitable temperatures.

The isolated solid may be recovered by any methods, including decantation, centrifugation, gravity filtration, suction filtration, or any other suitable techniques for the recovery of solids. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the asenapine maleate is not degraded in quality. The drying may be carried out for any desired times until the desired product quality is achieved.

The dried product may be subjected to a size reduction procedure to produce desired particle sizes. Size reduction may be performed before drying, or after the completion of drying of the product. Techniques that may be used for particle size reduction include, without limitation, ball, roller and hammer milling, or jet milling.

In an aspect, the present application provides processes for the preparation of a microcrystalline monoclinic form of asenapine maleate, comprising:

a) providing a solution of asenapine in a solvent;
b) combining the solution of asenapine obtained in step a) with a solution of maleic acid in a solvent; and
c) isolating the microcrystalline monoclinic form of asenapine maleate.

Step a) involves providing a solution of asenapine in a solvent. The solution of asenapine may be obtained by dissolving asenapine in a solvent, or it may be obtained directly from a reaction mixture, in which the compound is formed in the course of synthesis of asenapine. Any physical forms of asenapine, such as crystalline, amorphous, or their mixtures may be utilized for preparing the solution of asenapine in step a).

Solvents that may be employed for providing a solution of asenapine in step a) include, but are not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof. The temperatures at which a solution may be obtained in step a) range from about 0° C. to about the reflux temperature of the solvent that is used, or any other suitable temperatures.

Step b) involves combining the solution of asenapine obtained in step a) with a solution of maleic acid in a solvent. Alternatively, step b) may be conducted by adding a solution of asenapine to a solution of maleic acid, or adding a solution of maleic acid to a solution of asenapine.

Suitable solvents that may be used in step b) include, but are not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof. Suitable temperatures that may be used in step (b) may be less than about less than about 100° C., less than about 80° C., or less than about 60° C., or less than about 40° C., or less than about 30° C., or less than about 20° C., or less than about 10° C., or any other suitable temperatures.

Step c) involves isolating the microcrystalline monoclinic form of asenapine maleate. Isolation in step c) may involve any methods, including removal of solvent, cooling, concentrating the mass, using an anti-solvent, extraction with a solvent, adding seed crystals to induce crystallization, or the like. Stirring or other alternate methods such as shaking, agitation, or the like, may also be employed for the isolation. Suitable temperatures for isolation may be less than about 60° C., less than about 40° C., less than about 20° C., less than about 10° C., less than about 5° C., less than about 0° C., or any other suitable temperatures. The isolated solid may be recovered by any methods, including decantation, centrifugation, gravity filtration, suction filtration, or any other suitable techniques for the recovery of solids.

The isolated compound may be further purified by recrystallization one or more times from a suitable solvent, such as, but not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof; optionally involving the use of seed crystals of the monoclinic form. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the asenapine maleate is not degraded in quality. The drying may be carried out for any desired times until the desired product quality is achieved.

In an aspect, the present application provides processes for the preparation of a microcrystalline monoclinic form of asenapine maleate, comprising:

a) providing a solution of asenapine maleate in a solvent;
b) optionally, seeding the solution obtained in step a) with crystals of the monoclinic form; and
c) isolating the microcrystalline monoclinic form of asenapine maleate.

Step a) involves providing a solution of asenapine maleate in a solvent. The solution of asenapine maleate may be obtained by dissolving asenapine maleate in a solvent, or it may be obtained directly from a reaction mixture, in which the compound is formed in the course of synthesis of asenapine maleate. Any physical forms of asenapine maleate, such as crystalline, amorphous, or their mixtures may be utilized for preparing the solution of asenapine maleate in step a).

Solvents that may be employed for providing a solution of asenapine maleate in step a) include, but are not limited to: $C_3$-$C_9$ alcohol solvents, e.g., 2-propanol, 1-propanol, 1-butanol, 2-butanol, or the like; ester solvents, e.g., ethyl acetate, n-propyl acetate, n-butyl acetate, t-butyl acetate, or the like; or mixtures thereof. The temperatures at which a solution may be obtained in step a) range from about 0° C. to about the reflux temperature of the solvent that is used, or any other suitable temperatures.

Step b) involves optionally seeding the solution obtained in step a) with crystals of the monoclinic form. Crystals of the monoclinic form that are used in step b) may be obtained by any of the processes of the present application.

Step c) involves isolating the microcrystalline monoclinic form of asenapine maleate. Isolation in step c) may involve any methods, including removal of solvent, cooling, concentrating the mass, using an anti-solvent, extraction with a solvent, adding seed crystals to induce crystallization, or the like. Stirring or other alternate methods such as shaking, agitation, or the like, may also be employed for the isolation. Suitable temperatures for isolation may be less than about 60° C., less than about 40° C., less than about 20° C., less than about 10° C., less than about 5° C., less than about 0° C., less than about −10° C., less than about −20° C., or any other suitable temperatures.

The isolated solid may be recovered by any methods, including decantation, centrifugation, gravity filtration, suction filtration, or any other suitable techniques for the recovery of solids. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the asenapine maleate is not degraded in quality. The drying may be carried out for any desired times until the desired product quality is achieved.

Milling or micronization techniques that may be used for particle size reduction include, without limitation sifting, milling using mills, such as, for example, ball, roller and hammer mills, or jet mills, including, for example, air jet mills, or any other conventional techniques.

The particle sizes of a drug substance can influence biopharmaceutical properties of its pharmaceutical products. For example, the particle sizes of the drug substance affects drug product manufacturing and dissolution, and hence the bioavailability from formulated products. Since asenapine maleate dissolves in saliva, the particle sizes are important. When drug substance particles are small, shorter periods of time are required to achieve high dissolved concentrations. From this perspective, smaller particles are preferred. In addition, smaller particle sizes tend to improve the homogeneity of powder blends, which may result in improved uniformity of the drug content in a pharmaceutical product.

Particle size distributions of a monoclinic form of asenapine maleate, which is stable to micronization, particles may be measured using any techniques known in the art. For example, particle size distributions of asenapine maleate particles may be measured using microscopy or light scattering equipment, such as, for example, a Malvern Master Size 2000 from Malvern Instruments Limited, Malvern, Worcestershire, United Kingdom. The particle size distributions can be expressed, for example, in terms of d(90), d(50), and d(10) values, where the values (e.g., expressed in μm) are the maximum sizes for 90, 50, and 10 percent of the particles, respectively.

In an aspect, the present application provides processes for the preparation of a microcrystalline monoclinic form of asenapine maleate, comprising: micronizing a monoclinic form of asenapine maleate, which is stable to micronization, having particle size distributions where d(90) is at least 50 μm.

In an aspect, processes of the present application provide a stable, polymorphically pure, microcrystalline, monoclinic form of asenapine maleate.

In an aspect, the present application provides pharmaceutical compositions comprising a monoclinic form of asenapine maleate, which is stable to micronization, together with at least one pharmaceutically acceptable excipient. In an aspect, the present application provides pharmaceutical compositions comprising a microcrystalline monoclinic form of asenapine maleate, together with at least one pharmaceutically acceptable excipient.

In one aspect, the present application provides processes comprising reacting a cis-isomer of Formula IX, or a mixture of a cis-isomer of Formula IX and a trans-isomer of Formula X, with a suitable reagent to afford a mixture of cis-isomer of Formula IX and trans-isomer of Formula X enriched with trans-isomer of Formula X:

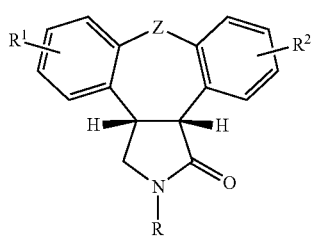

IX

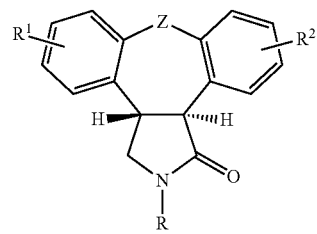

X wherein Z represents oxygen, sulfur, or a methylene group; R represents an $C_1$-$C_6$alkyl- or $C_7$-$C_{10}$(aryl)alkyl- group; $R^1$ and $R^2$ are each independently chosen from hydrogen, $C_1$-$C_6$alkyl, hydroxy, $C_1$-$C_6$alkoxy-, halo, nitro, amino, substituted amino, cyano, sulfonyl, carboxyl, substituted carboxy, or $CF_3$—.

A cis-isomer of Formula IX, or a mixture of a cis-isomer of Formula IX and a trans-isomer of Formula X, may be prepared using any processes known in the art. For example, it may be prepared by a process described for a mixture of cis- and trans-2-methyl-3,4,4a,13b-tetrahydrodibenz[2,3;6,7]oxepino[4,5-c]pyridin-1(2H)-one; or by a process described for trans-5-chloro-2,3,3a,12b-tetrahydro-2-methyl-1H-dibenz[2,3:6,7]oxepino[4,5-c]pyrrol-1-one and cis-5-chloro-2,3,3a,12b-tetrahydro-2-methyl-1H-dibenz[2,3:6,7]oxepino[4,5-c]pyrrol-1-one in Example 9E, page 9, paragraph [0048] of US 2006/0229352 A1, which is incorporated herein by reference in its entirety.

The resulting mixture of cis-isomer of Formula IX and trans-isomer of Formula X enriched with trans-isomer of Formula X obtained above may contain cis-isomer of Formula IX in amounts less than about 95%, less than about 90%, less than about 80%, less than about 70%, less than about 60%, less than about 50%, less than about 40%, less than about 30%, less than about 20%, less than about 10%, less than about 5%, less than about 4%, less than about 3%, less than about 2%, less than about 1%, less than about 0.5%, less than about 0.2%, less than about 0.1%, less than about 0.05%, by weight. Suitable reagents for the above reaction include, but are not limited to, triethylamine, diisopropylethylamine, 1,8-diazabicyclo[5.4.0]undec-7-ene (DBU), 1,5-diazabicyclo[4.3.0]non-5-ene (DBN), pyridine, morpholine, n-propylamine, sodium methoxide, other organic bases, potassium hydroxide, sodium hydroxide, potassium tert-butoxide, potassium hexamethyldisilazane, sodium hexamethyldisilazane, or the like, or any mixtures thereof.

The reaction of the cis-isomer of Formula IX, or a mixture of cis-isomer of Formula IX and trans-isomer of Formula X, with a suitable reagent may be optionally carried out in a suitable solvent, such as, for example, an alcohol solvent, a ketone solvent, an aromatic hydrocarbon solvent, a hydrocarbon solvent, a halogenated hydrocarbon solvent, an ester solvent, e.g., ethyl acetate, n-propyl acetate, n-butyl acetate, t-butyl acetate, or the like; an ether solvent, a polar aprotic solvent, a nitrile solvent, water, or any mixtures thereof.

Suitable temperatures that may be employed for the reaction of cis-isomer of Formula IX, or a mixture of cis-isomer of Formula IX and trans-isomer of Formula X, with a suitable reagent are less than about 100° C., less than about 80° C., less than about 60° C., less than about 40° C., less than about 20° C., less than about 0° C., or any other suitable temperatures. Suitable times for completing the reaction of the mixture of cis-isomer of Formula IX, or a cis-isomer of Formula IX and trans-isomer of Formula X, with a suitable reagent depend on the temperature and other conditions, and may be generally about 30 minutes, or about 1 hour, or about 3 hours, or about 5 hours, or about 10 hours, or about 15 hours, or about 20 hours, or about 25 hours, or about 30 hours, or about 40 hours, or longer.

The cis-isomer of Formula IX, or mixture of cis-isomer of Formula IX and trans-isomer of Formula X enriched with trans-isomer of Formula X, thus obtained may be separated by conventional separation techniques to afford a cis-isomer of Formula IX and trans-isomer of Formula X, or their mixture enriched in one of the isomers. Examples of separation techniques include, but are not limited to, chromatography, selective crystallization, or any other suitable techniques. The solvents used for separating cis-isomer of Formula IX and trans-isomer of Formula X include, but are not limited to, alcohol solvents, ketone solvents, aromatic hydrocarbon solvents, hydrocarbon solvents, halogenated hydrocarbon solvents, ester solvents, ether solvents, polar aprotic solvents, nitrile solvents, water, or any mixtures thereof.

A trans-isomer of Formula X, or mixture of cis-isomer of Formula IX and trans-isomer of Formula X enriched with trans-isomer of Formula X, may be further purified one or more times using any suitable techniques. For example, it may be purified by precipitation, slurrying in a suitable solvent, or any other suitable techniques. Precipitation may be achieved by crystallization, such as by cooling a solution, concentrating a solution, or by combining an anti-solvent with a solution of the product, or any other suitable methods. Anti-solvents are liquids in which trans-isomer of Formula X is poorly soluble. Suitable anti-solvents include, but are not limited to, hydrocarbon solvents, ether solvents, water, or any mixtures thereof; or any other suitable anti-solvents.

The resulting trans-isomer of Formula X, or mixture of cis-isomer of Formula IX and trans-isomer of Formula X enriched with trans-isomer of Formula X, may optionally be dried. This drying may be carried out in a tray dryer, vacuum oven, air oven, fluidized bed dryer, spin flash dryer, flash dryer, rotary dryer, cone dryer, rotary cone dryer, or the like. Drying may be carried out at temperatures less than about 100° C., less than about 60° C., less than about 40° C., or any other suitable temperatures, at atmospheric pressure or under reduced pressure, and in the presence or absence of an inert atmosphere such as nitrogen, argon, neon, or helium. The drying may be carried out for any desired time periods to achieve the desired quality of the product, such as, for example, about 1 to about 15 hours, or longer.

The trans-isomer of Formula X, or mixture of cis-isomer of Formula IX and trans-isomer of Formula X enriched with trans-isomer of Formula X, thus obtained may be optionally used for the preparation of compound of Formula XI or a mixture of cis-isomer of Formula XII and trans-isomer of Formula XI enriched with trans-isomer of Formula XI:

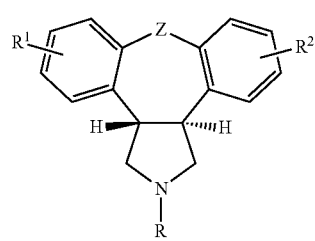

XI

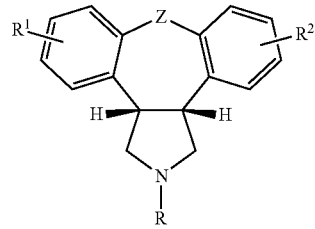

XII wherein R, R$^1$, R$^2$, and Z are as defined above.

Optionally, the cis-isomer of Formula IX, or mixture of cis-isomer of Formula IX and trans-isomer of Formula X enriched with cis-isomer of Formula IX, may be recovered from the mother liquors obtained after the separation using conventional processes known in the art, e.g., removal of solvent, cooling, concentrating the reaction mass, combining with an anti-solvent, extraction with a solvent, or the like. Stirring or other alternate methods such as shaking, agitation or the like may also be employed in the isolation. The solvents and anti-solvents were described above. The recovered cis-isomer of Formula IX, or mixture of cis-isomer of Formula IX and trans-isomer of Formula X enriched with cis-isomer of Formula IX, may be recycled by reacting with a suitable reagent, following the process as described above, to afford a trans-isomer of Formula X or a mixture of cis-isomer of Formula IX and trans-isomer of Formula X enriched with trans-isomer of Formula X.

Optionally, a mixture of cis-isomer of Formula IX and trans-isomer of Formula X enriched with trans-isomer of Formula X thus obtained may be recovered as a residue by conventional methods. The residue may be optionally dried. This drying may be carried out in a tray dryer, vacuum oven, air oven, fluidized bed dryer, spin flash dryer, flash dryer, rotary dryer, cone dryer, rotary cone dryer or the like. Drying may be carried out at temperatures less than about 100° C., less than about 60° C., less than about 40° C., or any other suitable temperatures, at atmospheric pressure or under reduced pressure, and in the presence or absence of an inert atmosphere such as nitrogen, argon, neon, or helium. The drying may be carried out for any desired time periods to achieve the desired quality of the product, such as, for example, about 1 to about 15 hours, or longer. The residue of cis-isomer of Formula IX and trans-isomer of Formula X enriched with trans-isomer of Formula X thus obtained may be optionally used without purification for the preparation of a compound of Formula XI or mixture of cis-isomer of Formula XII and trans-isomer of Formula XI enriched with trans-isomer of Formula XI.

Optionally, the mixture of cis-isomer of Formula IX and trans-isomer of Formula X enriched with trans-isomer of Formula X thus obtained may be directly used for the preparation of compound of Formula XI or mixture of cis-isomer of Formula XII and trans-isomer of Formula XI enriched with trans-isomer of Formula XI, without further isolation or conventional work-up.

In one aspect, the present application includes processes for preparing a compound of Formula XI and the pharmaceutically acceptable salts thereof:

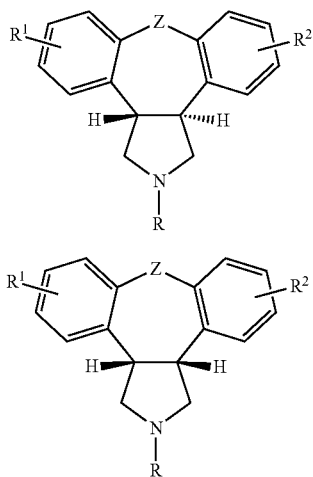

wherein R, R¹, R², and Z are as defined above, comprising one or more of the following steps, individually, or in the sequence recited:

a) reacting a cis-isomer of Formula IX, or a mixture of cis-isomer of Formula IX and trans-isomer of Formula X, with a suitable reagent to afford a mixture of cis-isomer of Formula IX and trans-isomer of Formula X enriched with trans-isomer of Formula X;

b) optionally, separating the trans-isomer of Formula X, or mixture of cis-isomer of Formula IX and trans-isomer of Formula X enriched with trans-isomer of Formula X, from the mixture obtained in a);

c) converting the trans-isomer of Formula X, or mixture of cis-isomer of Formula IX and trans-isomer of Formula X enriched with trans-isomer of Formula X, with a suitable reagent to afford a trans-isomer of Formula XI or a mixture of cis-isomer of Formula XII and trans-isomer of Formula XI enriched with trans-isomer of Formula XI; and d) optionally, converting the resulting trans-isomer of Formula XI, or mixture of cis-isomer of Formula XII and trans-isomer of Formula XI enriched with trans-isomer of Formula XI, to a salt thereof.

Step a) involves reacting a mixture of cis-isomer of Formula IX and trans-isomer of Formula X with a suitable reagent, to afford a mixture of cis-isomer of Formula IX and trans-isomer of Formula X enriched with trans-isomer of Formula X. The resulting mixture of cis-isomer of Formula IX and trans-isomer of Formula X enriched with trans-isomer of Formula X obtained in a) may contain cis-isomer of Formula IX in amounts less than about 95%, less than about 90%, less than about 80%, less than about 70%, less than about 60%, less than about 50%, less than about 40%, less than about 30%, less than about 20%, less than about 10%, less than about 5%, less than about 4%, less than about 3%, less than about 2%, less than about 1%, less than about 0.5%, less than about 0.2%, less than about 0.1%, or less than about 0.05%, by weight.

Suitable reagents for the reaction of step a) include, but are not limited to, triethylamine, diisopropylethylamine, 1,8-diazabicyclo[5.4.0]undec-7-ene (DBU), 1,5-diazabicyclo[4.3.0]non-5-ene (DBN), pyridine, morpholine, n-propylamine, any other organic base, sodium methoxide, potassium hydroxide, sodium hydroxide, potassium tert-butoxide, potassium hexamethyldisilazane, sodium hexamethyldisilazane, or the like, or any mixtures thereof.

Step a) may be optionally carried out in a suitable solvent, such as, for example, alcohol solvents, ketone solvents, aromatic hydrocarbon solvents, hydrocarbon solvents, halogenated hydrocarbon solvents, ester solvents, ether solvents, polar aprotic solvents, nitrile solvents, water, or any mixtures thereof. Suitable temperatures that may be employed for the reaction of a) are less than about 100° C., less than about 80° C., less than about 60° C., less than about 40° C., less than about 20° C., less than about 0° C., or any other suitable temperatures. Suitable times for completing the reaction of a) depend on the temperature and other conditions, and may be generally less than about 30 hours, less than about 20 hours, less than about 10 hours, less than about 5 hours, less than about 2 hours, less than about 1 hour, or any other suitable times. Longer times also are suitable.

Optionally, the mixture obtained from a) may be recovered as a residue by conventional methods. The residue may optionally be dried. This drying may be carried out in a tray dryer, vacuum oven, air oven, fluidized bed dryer, spin flash dryer, flash dryer, rotary dryer, cone dryer, rotary cone dryer or the like. Drying may be carried out at temperatures less than about 100° C., less than about 60° C., less than about 40° C., or any other suitable temperatures, at atmospheric pressure or under reduced pressure, and in the presence or absence of an inert atmosphere such as nitrogen, argon, neon, or helium. The drying may be carried out for any desired time periods to achieve the desired quality of the product, such as, for example, about 1 to about 15 hours, or longer.

The residue comprising a mixture cis-isomer of Formula IX and trans-isomer of Formula X enriched with trans-isomer of Formula X thus obtained may be optionally used for the preparation of trans-compound of Formula XI or a mixture of compound of formula XI and a cis-compound of Formula XII.

Optionally, the mixture obtained from a) may be directly used for the preparation of a compound of Formula XI or a mixture of compound of formula XI and a cis-compound of Formula XII, without further isolation or conventional work-up.

Step b) involves optionally separating the trans-isomer of Formula X, or a mixture of cis-isomer of Formula IX and trans-isomer of Formula X enriched with trans-isomer of Formula X, from the mixture of a). The mixture obtained from a) may be separated using conventional separation techniques, to afford a cis-isomer of Formula IX and trans-isomer of Formula X. The separation techniques may involve chromatography, crystallization using a solvent or mixture of solvent, or any other suitable techniques. The solvents used for separation of cis-isomer of Formula IX and trans-isomer of Formula X may include, but are not limited to, alcohol solvents, ketone solvents, aromatic hydrocarbon solvents, hydrocarbon solvents, halogenated hydrocarbon solvents, ester solvents, ether solvents, polar aprotic solvents, nitrile solvents, water, or any mixtures thereof.

Optionally, a trans-isomer of Formula X may be further purified one or more times using any suitable techniques. For example, a trans-isomer of Formula X may be purified by precipitation, slurrying in a suitable solvent, or any other suitable techniques. The precipitation may be achieved by crystallization, such as by cooling a solution or by combining a solution of the product with an anti-solvent, or any other suitable methods known in the art. Anti-solvents are liquids in which trans-isomer of Formula X is poorly soluble. Suitable anti-solvents include, but are not limited to, hydrocarbon solvents, ether solvents, water, or any mixtures thereof; or any other suitable anti-solvents.

Optionally, the mixture obtained from a) may be separated using conventional separation techniques to afford a cis-isomer of Formula IX and a trans-isomer of Formula X, or their mixture enriched in one of the isomers. The separation techniques include but are not limited to, chromatography, selective crystallization, or any other suitable techniques. The solvents used for the separation of cis-isomer of Formula IX and trans-isomer of Formula X include, but are not limited to, alcohol solvents, ketone solvents, aromatic hydrocarbon solvents, hydrocarbon solvents, halogenated hydrocarbon solvents, ester solvents, ether solvents, polar aprotic solvents, nitrile solvents, water, or any mixtures thereof.

The resulting cis-isomer of Formula IX, trans-isomer of Formula X, or the mixture enriched in one of the isomers may optionally be dried. This drying may be carried out at temperatures less than about 100° C., less than about 60° C., less than about 40° C., or any other suitable temperatures, at atmospheric pressure or under reduced pressure, and in the presence or absence of an inert atmosphere such as nitrogen, argon, neon, or helium. The drying may be carried out for any desired time periods to achieve the desired quality of the product, such as, for example, about 1 to about 15 hours, or longer.

Optionally, a cis-isomer of Formula IX, or a mixture of cis-isomer of Formula IX and trans-isomer of Formula X enriched with cis-isomer of Formula IX, may be recovered from the mother liquors obtained after the separation by conventional processes, e.g., removal of solvent, cooling, concentrating the mass, combining with an anti-solvent, extraction with a solvent, or the like. Stirring or other alternate methods such as shaking, agitation or the like may also be employed for isolation. The solvent and anti-solvent may any of those described hereinabove. The recovered cis-isomer of Formula IX, or mixture of cis-isomer of Formula IX and trans-isomer of Formula X enriched with cis-isomer of Formula IX, may be recycled by reacting with a suitable reagent, following the process as described above, to afford a trans-isomer of Formula X or a mixture of cis-isomer of Formula IX and trans-isomer of Formula X enriched with trans-isomer of Formula X.

Optionally, the trans-isomer of Formula X, or mixture of cis-isomer of Formula IX and trans-isomer of Formula X enriched with trans-isomer of Formula X, thus obtained may be directly used, without purification, for the preparation of a compound of Formula XI or a mixture of cis-isomer of Formula XII and trans-isomer of Formula XI enriched with trans-isomer of Formula XI.

Step c) involves converting the trans-isomer of Formula X, or mixture of cis-isomer of Formula IX and trans-isomer of Formula X enriched with trans-isomer of Formula X, with a suitable reagent to afford a trans-isomer of Formula XI or a mixture of cis-isomer of Formula XII and trans-isomer of Formula XI enriched with trans-isomer of Formula XI.

Step c) may be carried out using any suitable techniques, including, for example, reduction. Suitable reduction techniques, which may be used in step c), include, but are not limited to, metal mediated reduction, such as with zinc and acetic acid, zinc and hydrochloric acid, iron and acetic acid, or any other suitable metal reducing agents; reacting with a reducing agent, such as lithium aluminum hydride, diborane, sodium borohydride in acidic conditions, sodium dihydro-bis (2-methoxyethoxy) aluminate solution (VITRIDE®); and catalytic hydrogenation in the presence of catalysts such as Raney™ nickel, palladium on carbon, rhodium, or the like; combinations thereof; or any other suitable reducing techniques.

Suitable solvents that may be used include, but are not limited to, alcohol solvents, ketone solvents, aromatic hydrocarbon solvents, hydrocarbon solvents, halogenated hydrocarbon solvents, ester solvents, ether solvents, polar aprotic solvents, water, or any mixtures thereof. Step c) may be carried out at suitable temperatures less than about 150° C., less than about 100° C., less than about 60° C., less than about 40° C., or any other suitable temperatures. Suitable times for completing the reaction in step c) depend on temperature and other conditions and may be generally less than about 15 hours, less than about 10 hours, less than about 5 hours, less than about 2 hours, less than about 30 minutes, or any other suitable times. Longer times also are useful.

The resulting compound of Formula XI may be recovered using any methods known in the art. For example, it may be isolated by a method that includes but is not limited to, filtration by gravity or suction, centrifugation, slow evaporation, or the like. Optionally, the product of step c) may be directly used in step d) without further isolation or after conventional work-up, such as, for example, quenching the reaction mixture with a quenching agent and extracting the product into a solvent.

Step d) involves optionally converting the resulting trans-isomer of Formula XI, or mixture of cis-isomer of Formula XII and trans-isomer of Formula XI enriched with trans-isomer of Formula XI, to a pharmaceutically acceptable salt thereof. Step d) may be carried out using any processes known in the art. For example, step d) may be carried out by reacting with a pharmaceutically acceptable acid in a suitable solvent, to obtain the corresponding acid addition salt. Step d) may be carried out in a suitable solvent, such as, for example, alcohol solvents, ketone solvents, aromatic hydrocarbon solvents, hydrocarbon solvents, halogenated hydrocarbon solvents, ester solvents, ether solvents, polar aprotic solvents, nitrile solvents, water, any mixtures thereof; or any other suitable solvents. The salt of trans-isomer of Formula XI, or mixture of a salt of cis-isomer of Formula XII and salt of trans-isomer of Formula XI enriched with salt of trans-isomer of Formula XI, resulting from step d) may be isolated as a crystalline compound, a solvate, an amorphous compound, or a mixture thereof, as desired.

The salt of a trans-isomer of Formula XI, or a mixture of salts of a cis-isomer of Formula XII and a trans-isomer of Formula XI enriched with salt of trans-isomer of Formula XI, resulting from step d) may be isolated using any processes known in the art. For example, it may be isolated by a method that includes filtration by gravity or suction, centrifugation, slow evaporation, or drying, which may be suitably carried out using techniques including tray drying, vacuum drying, air drying, fluidized bed drying, spin flash drying, flash drying, spray drying, thin film drying, freeze drying, or the like, at atmospheric pressure or under reduced pressure.

The isolated, solid salt of a trans-isomer of Formula XI, or mixture of salts of cis-isomer of Formula XII and trans-isomer of Formula XI enriched with salt of trans-isomer of Formula XI, may carry a portion of occluded mother liquor containing higher levels of impurities. If desired the isolated solid may be washed with a solvent to wash out the mother liquor.

The isolated solid may be dried. This drying may be carried out in a tray dryer, vacuum oven, air oven, fluidized bed dryer, spin flash dryer, flash dryer, rotary dryer, cone dryer, rotary cone dryer or the like. Drying may be carried out at temperatures less than about 100° C., less than about 60° C., less than about 40° C., or any other suitable temperatures, at atmospheric pressure or under reduced pressure, and in the presence or absence of an inert atmosphere such as nitrogen, argon, neon, or helium. The drying may be carried out for any desired time period to achieve the desired quality of the product, such as, for example, about 1 to about 15 hours, or longer.

In embodiments, processes of the present application provide asenapine maleate having purity by HPLC which is essentially pure, substantially pure, or even pure.

In embodiments, processes of the present application provide asenapine maleate substantially free of one or more of its corresponding impurities.

The occurrence of different crystal forms (polymorphism) is a property of some molecules and molecular complexes. A single molecule may give rise to a variety of solids having distinct physical properties such as melting point, X-ray diffraction pattern, infrared absorption fingerprint, and NMR spectrum. This variation in solid forms may be significant and may result in differences with respect to bioavailability, stability, and other differences for formulated pharmaceutical products. Because polymorphic forms can vary in their physical properties, regulatory authorities require that efforts shall be made to identify all polymorphic forms, e.g., crystalline, amorphous, solvated, etc., of new drug substances.

The differences in the physical properties of polymorphs result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family. One of the most important physical properties of pharmaceutical polymorphs is their solubility.

The existence and possible numbers of polymorphic forms for a given compound cannot be predicted, and there are no "standard" procedures that can be used to prepare polymorphic forms of a substance. However, new forms of a pharmaceutically useful compound may provide an opportunity to improve the performance characteristics of pharmaceutical products. Further, discovery of additional polymorphic forms, including solvate polymorphs, may help in the identification of the polymorphic content of a batch of an active pharmaceutical ingredient. For example, in some cases, different forms of the same drug can exhibit very different solubility and dissolution rates.

Crystalline forms are characterized by scattering techniques, e.g., x-ray diffraction powder pattern, by spectroscopic methods, e.g., infra-red, $^{13}C$ nuclear magnetic resonance spectroscopy, and by thermal techniques, e.g., differential scanning calorimetry or differential thermal analysis. The compound of this invention is best characterized by the X-ray powder diffraction pattern determined in accordance with procedures that are known in the art. For a discussion of these techniques see J. Haleblian, *J. Pharm. Sci.* 1975 64:1269-1288, and J. Haleblian and W. McCrone, *J. Pharm. Sci.* 1969 58:911-929. A polymorphic form may be described by reference to patterns, spectra, or other graphical data as "substantially" as shown or depicted in a drawing, or by one or more data points. It will be appreciated that patterns, spectra, and other graphical data can have minor shifts in their positions, relative intensities, or other values due to a number of factors known to those of skill in the art. For example, in the crystallographic and powder X-ray diffraction arts, some variations in peak positions or the relative intensities of one or more peaks of a pattern can occur because of, without limitation, the equipment used, the sample preparation protocol, preferred packing and orientations, the radiation source, operator error, method and length of data collection, and the like. However, those of ordinary skill in the art will be able to compare the figures herein with patterns, etc. generated for an unknown form of, in this case, asenapine maleate, and confirms its identity as a form discussed herein. The same holds true for other techniques which may be reported herein.

In addition, where a reference is made to a drawing, it is permissible to, and this document includes and contemplates, the selection of any number of data points illustrated in the drawing that uniquely define that crystalline form, within any associated and recited margins of error, for purposes of identification.

Generally, a diffraction angle (2θ) in powder X-ray diffractometry may have a permissible variation in the range of ±0.2°. Therefore, the aforementioned diffraction angle values should be understood as including values in the range of about ±0.2°. Accordingly, the present invention includes not only crystals whose peak diffraction angles in powder X-ray diffractometry completely coincide with each other, but also crystals whose peak diffraction angles coincide with each other with a permissible variation of about ±0.2°. Therefore, in the present specification, the phrase "having a diffraction peak at a diffraction angle (2θ±0.2°) of 7.9°" means "having a diffraction peak at a diffraction angle (2θ) of 7.7° to 8.1°". Although the intensities of peaks in the x-ray powder diffraction patterns of different batches of a compound may vary slightly, the peaks and the peak locations are characteristic for a specific polymorphic form. The relative intensities of the PXRD peaks can vary depending on the sample preparation technique, crystal size distribution, various filters used, the sample mounting procedure, and the particular instrument employed. Moreover, instrument variation and other factors can affect the 2-theta values. Moreover, new peaks may be observed or existing peaks may disappear, depending on the type of the machine or the settings (for example, whether a Ni filter is used or not).

Where a reference is made to a drawing, it is permissible to, and this document includes and contemplates, the selection of any number of data points illustrated in the drawing that uniquely define that crystalline form, within any associated and recited margins of error, for purposes of identification.

All percentages and ratios used herein are by weight of the total composition and all measurements made are at about 25° C. and about normal pressure, unless the context requires otherwise. All temperatures are in degrees Celsius unless specified otherwise. As used herein, "comprising" (open-ended) means the element or elements recited, or their equivalents in structure or function, plus any other element or elements which are not recited. The terms "having" and "including" are also to be construed as open-ended. As used herein, "consisting essentially of" means that the application may include elements in addition to those recited in the claim, but only if the additional elements do not materially alter the basic and novel characteristics. All ranges recited herein include the endpoints, including those that recite a range "between" two values. Whether so indicated or not, all values recited herein are approximate as defined by the circumstances, including the degree of expected experimental error, technique error, and instrument error for a given technique used to measure a value.

In an aspect, the present application provides pharmaceutical compositions comprising a stable, polymorphically pure monoclinic form of asenapine maleate, together with at least one pharmaceutically acceptable excipient.

In an aspect, the present application provides pharmaceutical compositions comprising a stable, polymorphically pure microcrystalline monoclinic form of asenapine maleate, together with at least one pharmaceutically acceptable excipient.

Asenapine maleate together with at least one pharmaceutically acceptable excipient of the present application may be formulated as: solid oral dosage forms such as, but not limited to: powders, granules, pellets, tablets, and capsules; liquid oral dosage forms such as but not limited to syrups, suspensions, dispersions, and emulsions; and injectable preparations such as but not limited to solutions, dispersions, and freeze-dried compositions. Formulations may be in the forms of immediate release, delayed release, or modified release. Further, immediate release compositions may be conventional, dispersible, chewable, mouth dissolving, or flash melt preparations, and modified release compositions may comprise hydrophilic or hydrophobic, or combinations of hydrophilic and hydrophobic, release rate controlling substances to form matrix, reservoir, or combinations of matrix and reservoir systems. The compositions may be prepared using any techniques such as direct blending, dry granulation, wet granulation, and extrusion and spheronization. Compositions may be presented as uncoated, film coated, sugar coated, powder coated, enteric coated, and modified release coated.

DEFINITIONS

The following definitions are used in connection with the present application unless the context indicates otherwise. The acronym DMF means N,N-dimethyl formamide and HPLC is high pressure liquid chromatography. An "alcohol solvent" is an organic solvent containing a carbon bound to a hydroxyl group. "Alcohol solvents" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, $C_{1-6}$alcohols, or the like.

"Alkoxy-" refers to the group R—O— where R is an alkyl group, as defined below. Exemplary $C_1$-$C_6$alkoxy- groups include, but are not limited to, methoxy, ethoxy, n-propoxy, 1-propoxy, n-butoxy, and t-butoxy. An alkoxy group can be unsubstituted or substituted with one or more of the following groups: halogen, hydroxyl, $C_1$-$C_6$alkoxy-, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$-carboxyamidoalkyl-, or $O_2N$—.

"Alkyl-" refers to a hydrocarbon chain that may be a straight chain or branched chain, containing the indicated number of carbon atoms, for example, a $C_1$-$C_{10}$alkyl- group may have from 1 to 10 (inclusive) carbon atoms in it. In the absence of any numerical designation, "alkyl" is a chain (straight or branched) having 1 to 6 (inclusive) carbon atoms in it. Examples of $C_1$-$C_6$alkyl- groups include, but are not limited to, methyl, ethyl, propyl, butyl, pentyl, hexyl, isopropyl, isobutyl, sec-butyl, tert-butyl, isopentyl, neopentyl, and isohexyl. An alkyl- group can be unsubstituted or substituted with one or more of the following groups: halogen, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, hydroxyl, $C_1$-$C_6$alkoxy-, $C_1$-$C_6$alkyl-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$-carboxyamidoalkyl-, or $O_2N$—.

"Aromatic hydrocarbon solvent" refers to a liquid, unsaturated, cyclic, hydrocarbon containing one or more rings which has at least one 6-carbon ring containing three double bonds. It is capable of dissolving a solute to form a uniformly dispersed solution. Examples of an aromatic hydrocarbon solvent include, but are not limited to, benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$aromatic hydrocarbons, or mixtures thereof.

"Aryl-" refers to an aromatic hydrocarbon group. Examples of an $C_6$-$C_{14}$aryl- group include, but are not limited to, phenyl, 1-naphthyl, 2-naphthyl, 3-biphen-1-yl, anthryl, tetrahydronaphthyl, fluorenyl, indanyl, biphenylenyl, and acenaphthenyl. An aryl group can be unsubstituted or substituted with one or more of the following groups: $C_1$-$C_6$alkyl-, halogen, haloalkyl-, hydroxyl, hydroxyl($C_1$-$C_6$alkyl)-, $H_2N$—, amino($C_1$-$C_6$alkyl)-, di($C_1$-$C_6$alkyl)amino-, $HO_2C$—, ($C_1$-$C_6$alkoxy)carbonyl-, ($C_1$-$C_6$alkyl)carboxyl-, di($C_1$-$C_6$alkyl)amido-, $H_2$NC(O)—, ($C_1$-$C_6$alkyl)amido-, or $O_2N$—.

"(Aryl)alkyl-" refers to an alkyl group, as defined above, wherein one or more of the alkyl group's hydrogen atoms have been replaced with an aryl group as defined above. $C_7$-$C_{10}$(Aryl)alkyl-moieties include benzyl, 1-phenylethyl, 2-phenylethyl, 3-phenylpropyl, 2-phenylpropyl, or the like. An (aryl)alkyl group can be unsubstituted or substituted with one or more of the following groups: halogen, $H_2N$—, hydroxyl, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, hydroxyl, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cyclo alkyl-, $C_1$-$C_6$haloalkyl-, amino($C_1$-$C_6$alkyl)-, ($C_1$-$C_6$alkyl)carboxyl-, $C_1$-$C_6$carboxyamido alkyl-, or $O_2N$—.

An "ester solvent" is an organic solvent containing a carboxyl group —(C═O)—O— bonded to two other carbon atoms. "Ester solvents" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, $C_3$-6esters, or the like.

An "ether solvent" is an organic solvent containing an oxygen atom —O-bonded to two other carbon atoms. "Ether solvents" include, but are not limited to, diethyl ether, diisopropyl ether, methyl t-butyl ether, glyme, diglyme, tetrahydrofuran, 2-methyltetrahydrofuran, 1,4-dioxane, dibutyl ether, dimethylfuran, 2-methoxyethanol, 2-ethoxyethanol, anisole, $C_{2-6}$ethers, or the like.

A "ketone solvent" is an organic solvent containing a carbonyl group —(C═O)— bonded to two other carbon atoms. "Ketone solvents" include, but are not limited to, acetone, ethyl methyl ketone, diethyl ketone, methyl isobutyl ketone, $C_{3-6}$ketones, or the like.

"Halo" or "halogen" refers to fluorine, chlorine, bromine, or iodine.

A "halogenated hydrocarbon solvent" is an organic solvent containing a carbon bound to a halogen. "Halogenated hydrocarbon solvents" include, but are not limited to, dichloromethane, 1,2-dichloroethane, trichloroethylene, perchloroethylene, 1,1,1-trichloroethane, 1,1,2-trichloroethane, chloroform, carbon tetrachloride, or the like.

A "hydrocarbon solvent" refers to a liquid, saturated hydrocarbon, which may be linear, branched, or cyclic. It is capable of dissolving a solute to form a uniformly dispersed solution. Examples of a hydrocarbon solvent include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, and mixtures thereof.

The term "microcrystalline" as used herein refers to a crystalline solid that comprises particles having size distributions where d(90) is less than or equal to about 50 μm, about 45 μm, about 35 μm, about 25 μm, about 15 μm, or about 5 μm.

The term "micronization" as used herein refers to the process of reducing the average diameter of a solid material's particles. The term micronization is used when the particles that are produced are only a few micrometers in diameter. Techniques that may be used for micronization include, without limitation sifting, milling using mills, such as, for example, ball, roller, impact, or hammer mills; or jet mills, including, for example, air jet mills or jet pulverizers, or any other conventional techniques.

A "nitrile solvent" is an organic solvent containing a cyano —(C≡N) bonded to another carbon atom. "Nitrile solvents" include, but are not limited to, acetonitrile, propionitrile, $C_{2-6}$ nitriles, or the like.

An "organic base" is an organic compound, which acts as a base. Examples of such bases include, but are not limited to, triethylamine, diisopropylamine, Hunig's base, DABCO, triethanolamine, tributylamine, pyridine, lutidine, 4-dimethylamino pyridine (DMAP), diethanolamine, 4-methylmorpholine, dimethylethanolamine, tetra methylguanidine, morpholine, imidazole, 2-methylimidazole, 4-methylimidazole, tetra methylammonium hydroxide, tetraethylammonium hydroxide, N-methyl-1,5,9-triazabicyclo[4.4.0]decene, 1,8-diazabicyclo[5.4.0]undec-7-ene (DBU), dicyclo hexylamine, and picoline.

Representative "pharmaceutically acceptable acids" include, but are not limited to, those capable of making water-soluble and water-insoluble salts, such as the acetate, 4-acetylaminobenzoate, ascorbate, benzenesulfonate, benzoate, bicarbonate, bisulfate, bitartrate, borate, butyrate, camsylate (camphorsulfonate), carbonate, citrate, clavulariate, dihydrochloride, diphosphate, edisylate (camphorsulfonate), esylate (ethanesulfonate), formate, fumarate, gluceptate (glucoheptonate), gluconate, glucuronate, glutamate, glycolate, hexafluorophosphate, hexylresorcinate, hydrobromide, hydrochloride, hydroxynaphthoate, 1-hydroxy-2-naphthoate, 3-hydroxy-2-naphthoate, hydroiodide, hydrofluoride, isobutyrate, isopropanolate, isothionate (2-hydroxyethanesulfonate), lactate, lactobionate, laurate, lauryl sulfate, malate, maleate, malonate, mandelate, 2-methoxyphenylacetate, mesylate, mucate, napsylate, nitrate, oleate, oxalate, palmitate, pamoate (4,4'-methylenebis-3-hydroxy-2-naphthoate, or embonate), pantothenate, phosphate, picrate, propionate, p-toluenesulfonate, salicylate, stearate, subacetate, succinate, sulfate, sulfosaliculate, suramate, tannate, tartrate, and valerate salts.

A "polar aprotic solvent" has a dielectric constant greater than 15 and is at least one selected from the group consisting of amide-based organic solvents, such as N,N-dimethylformamide (DMF), N,N-dimethylacetamide (DMA), N-methylpyrrolidone (NMP), formamide, acetamide, propanamide, hexamethyl phosphoramide (HMPA), and hexamethyl phosphorus triamide (HMPT); nitro-based organic solvents, such as nitromethane, nitroethane, nitropropane, and nitrobenzene; pyridine-based organic solvents, such as pyridine and picoline; sulfone-based solvents, such as dimethylsulfone, diethylsulfone, diisopropylsulfone, 2-methylsulfolane, 3-methylsulfolane, 2,4-dimethylsulfolane, 3,4-dimethy sulfolane, 3-sulfolene, and sulfolane; and sulfoxide-based solvents such as dimethylsulfoxide (DMSO).

Polymorphs are different solids sharing the same molecular formula, yet having distinct physical properties when compared to other polymorphs of the same formula. As used throughout the disclosure, the D(10), D(50), and D(90) values are useful ways for indicating a particle size distribution. D(90) refers to at least 90 volume percent of the particles having a size smaller than the said value. Likewise, D(10) refers to 10 volume percent of the particles having a size smaller than the said value. D(50) refers to 50 volume percent of the particles having a size smaller than the said value. Methods for determining D(10), D(50), and D(90) include laser diffraction, such as using equipment from Malvern Instruments Ltd. of Malvern, Worcestershire, United Kingdom. HPLC is High Pressure Liquid Chromatography.

The term "enriched" should be understood to mean that the products obtainable in accordance with the process of present application have a higher content of one isomer, relative to the isomeric content of same isomer in a mixture before reacting the mixture with a suitable reagent.

Unless specified otherwise, the word "pure" as used herein means that the material is at least about 99% pure. In general, this refers to purity with regard to unwanted residual solvents, reaction by-products, impurities, and unreacted starting materials. In the case of stereoisomers, "pure" as used herein also means 99% of one enantiomer or diastereomer, as appropriate. "Substantially pure" as used herein means at least about 98% pure and, likewise, "essentially pure" as used herein means at least about 95% pure.

The term "polymorphically pure" as used herein, unless otherwise defined refers to the monoclinic crystalline form of asenapine maleate containing less than about 10%, or less than about 5%, or less than about 3%, or less than about 2%, or less than about 1%, or less than about 0.5%, or less than about 0.1%, or less than about 0.05%, or less than about 0.01%, or no detectable amount, of another crystalline form, as measured by PXRD analysis.

The term "stable" as used herein, unless otherwise defined, refers to the monoclinic crystalline form of asenapine maleate being retained during particle size reduction procedures. In embodiments, micronization of a monoclinic form of asenapine maleate, which is stable to micronization, prepared as described herein, reproducibly forms a microcrystalline product that retains the asenapine maleate monoclinic form.

All percentages and ratios used herein are by weight of the total composition and all measurements made are at about 25° C. and about atmospheric pressure, unless otherwise designated. All temperatures are in degrees Celsius unless specified otherwise. As used herein, "comprising" (open ended) means the elements recited, or their equivalent in structure or function, plus any other element or elements that are not recited. The terms "having" and "including" are also to be construed as open ended. As used herein, "consisting essentially of" means that the material may include ingredients in addition to those recited, but only if the additional ingredients do not materially alter the basic and novel characteristics of the material. All ranges recited herein include the endpoints, including those that recite a range "between" two values. Terms such as "about," "generally," "substantially," and the like are to be construed as modifying a term or value such that it is not an absolute. Such terms will be defined by the circumstances or the terms that they modify as those terms are understood by those of skill in the art. This includes the degree of expected experimental error, technique error, and instrument error for a given technique used to measure a value.

Throughout this disclosure, compounds represented by structural formulas having a pair of bold and hashed wedged bonds shall refer to "trans" diastereomers. Formulas with a pair of bold wedged bonds shall refer to "cis" diastereomers.

"Substantially free of one or more of its corresponding impurities" as used herein, unless otherwise defined refers to the compound that contains less than about 2%, or less than about 1%, or less than about 0.5%, or less than about 0.3%, or less than about 0.2%, or less than about 0.1%, or less than about 0.05%, or less than about 0.03%, or less than about 0.01%, by weight, of each individual

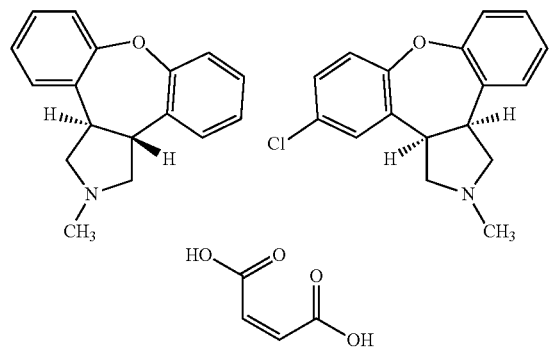

impurity including, without limitation, the deschloro asenapine of formula (XIII), cis asenapine of formula (XIV), tetrahydro asenapine maleate of formula (XV), amide compound of formula (XVI), n-oxide of formula (XVII), or any other drug-related or process-related impurity, and that contains a total amount of impurities of less than about 2%, or less than about 1%, or less than about 0.5%, or less than about 0.3%, or less than about 0.2%, or less than about 0.1%, or less than about 0.05% by weight.

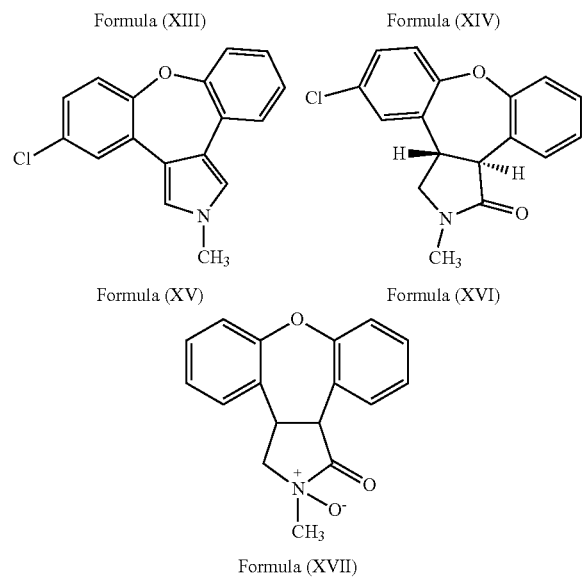

A high performance liquid chromatography method for the analysis of asenapine maleate utilizes a C18 or equivalent column. Additional parameters are as shown in Table 4.

TABLE 4

| | |
|---|---|
| Flow | 1.2 mL/min |
| Detector | 215 nm |
| Injection volume | 10.0 µl |
| Temperature | 45° C. |
| Mobile phase preparation | Buffer: Take 1000 ml MQ Water, add 2 ml OPA, and add 0.68 g of tetrabutyl ammonium hydrogen sulfate. A: Buffer:Acetonitrile - 90:10. B: Buffer:Methanol - 10:90. |
| Diluent | Acetonitrile:water (1:9) |
| Elution | Gradient |

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present invention. While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

All PXRD data reported herein are obtained using a Bruker AXS D8 Advance Powder X-ray Diffractometer or a PANalytical X-ray Diffractometer, using copper Kα radiation. Generally, a diffraction angle (2θ) in powder X-ray diffractometry may have permissible variation in the range of ±0.2°. Although the intensities of peaks in the x-ray powder diffraction patterns of different batches of a compound may vary slightly, the peaks and the peak locations are characteristic for a specific polymorphic form. The relative intensities of the PXRD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of PXRD is meant to encompass that peak assignments can vary by plus or minus about 0.2° 2-theta. Differential scanning calorimetric analyses reported herein are carried out using a DSC Q1000 model from TA Instruments with a ramp of 10° C./minute from 20° C. up to 200° C. Thermogravimetric analyses are performed using a model TGA Q500 from TA Instruments. The thermograms are recorded from 20 to 200° C. under a nitrogen gas purge at a flow of 40 mL/minute for the balance and 60 mL/minute for the sample, with a heating rate of 10° C./minute.

Example 1

Preparation of 2-(4-chlorophenoxy)-benzene acetic acid

To a solution of o-chlorophenylacetic acid (330 g) in o-xylene (4000 mL) is added 4-chlorophenol (306 g), $K_2CO_3$ (354 g), and copper powder (18 g) at 25-30° C. The mixture is heated at reflux for 2-3 hours and water is removed by azeotropic distillation. The reaction mixture is maintained for 1-2 hours at 25-30° C. and water (4000 mL) is added. Organic and aqueous layers are separated and the organic layer is washed with water (4000 mL). The pH of combined aqueous layers is adjusted to 1-1.5 by addition of aqueous HCl (100 mL) at 0-5° C. The formed solid is collected by filtration, washed with water (3000 mL) and hexane (500 mL), and then is dried to afford the title compound. Yield: 465 g. Purity by HPLC: 97.81%.

Example 2

Preparation of ethyl-N-[2-[2-(4-chlorophenoxy)phenyl]acetyl]-n-methylglycinate

To a solution of 2-(4-chlorophenoxy)-benzeneacetic acid (250 g) in toluene (700 mL) is slowly added a solution of $SOCl_2$ (105 mL) in a mixture of toluene (114 mL) and DMF (20 mL) at 40-50° C. over 1-2 hours. The solvent is evaporated under vacuum at 40-50° C. to afford a residue and any residual solvent is removed by adding and evaporating toluene (2×500 mL). The residue is dissolved in toluene (400 mL) and a solution of sarcosine ethyl ester hydrochloride and triethylamine (475 mL) in a mixture of DMF (1250 mL) and toluene (250 mL) is added at 0-5° C. The reaction mixture is maintained at 25-30° C. for 2-3 hours and water (2500 mL) is added. Organic and aqueous layers are separated and the aqueous layer is washed with toluene (250 mL). The combined organic layer is washed with saturated brine solution (1000 mL). After drying over anhydrous sodium sulfate, the solvent is removed under vacuum to afford the title compound as a residue, which is used for the next reaction step without further purification. Yield: 265.0 g. Purity by HPLC: 80.47%.

Example 3

Preparation of 3-(2-(4-chlorophenoxy)phenyl)-1-methylpyrrolidine-2,4-dione

To a suspension of potassium tert-butoxide (88 g) in toluene (1000 mL) is added a solution of ethyl-N-[2-[2-(4-chlorophenoxy)phenyl]acetyl]-N-methylglycinate (250 g) in toluene (1000 mL), under nitrogen at 15-25° C. and the mixture is maintained for 12-15 hours at 25-30° C. Water (3000 mL) is added and the mass is maintained for 1-2 hours at 0-5° C. Organic and aqueous layers are separated and the organic layer is washed with water (1000 mL). Aqueous layers are combined and washed with ethyl acetate (2000 mL). The pH of combined aqueous layers is adjusted to 2-2.5 by addition of aqueous HCl (100 mL) at 0-5° C. The solid is collected by filtration and washed with water (200 mL), then is dried to afford the crude title compound. The crude compound is further purified by heating at reflux a solution of crude 3-(2-(4-chlorophenoxy)phenyl)-1-methylpyrrolidine-2,4-dione in toluene (3600 mL) for 30-60 minutes, followed by cooling to room temperature. Solid that forms is collected by filtration, washed with hexane (500 mL), and dried to afford a purified title compound. Yield: 130 g. Purity by HPLC: 99.48%.

Example 4

Preparation of 5-chloro-2,3-dihydro-2-methyl-1H-dibenz[2,3;6,7]oxepino[4,5-c]pyrrol-1-one Phosphorus pentoxide (270 g) is added in portions to $H_3PO_4$ (270 g) and the mixture is maintained for 1-2 hours at 100-120° C. 3-(2-(4-chlorophenoxy)phenyl)-1-methyl-pyrrolidine-2,4-dione (90 g) is added and the mixture is maintained for three days at 100-110° C. Additional $P_2O_5$ (30 g) is added in two portions and the mass is maintained for one day at 100-120° C. The mass is poured into water (900 mL) and the mass is stirred overnight at 25-35° C. The mass is extracted with dichloromethane (1000 mL), the layers are separated, and the aqueous layer is washed with dichloromethane (400 mL). The combined organic layer is washed with water (900 mL), 5% sodium bicarbonate (300 mL), and saturated brine solution (500 mL). After drying over anhydrous sodium sulfate, the solvent is removed under vacuum. The residue is dissolved in methanol (400 ml) and heated at reflux for 30-60 minutes. The solution is cooled to −10 to −15° C. and a solid forms. The solid is collected by filtration, washed with chilled methanol (50 mL), and dried to afford the title compound. Yield: 37.5 g. Purity by HPLC: 89.47%.

Example 5

Preparation of cis-5-chloro-2,3,3a,12b-tetrahydro-2-methyl-1H-dibenz[2,3:6,7]oxepino[4,5-c]pyrrol-1-one Magnesium (15.6 g) is added to a solution of 5-chloro-2,3-dihydro-2-methyl-1H-dibenz[2,3;6,7]oxepino[4,5-c]pyrrol-1-one (50 g) in methanol (3000 mL), at 25-30° C. over 30-45 minutes. The mixture is heated at reflux for 30-45 minutes and, over a period of 1-2 hours, additional portions of magnesium (4×3 g) are added at 60-65° C. The mass is cooled, and water (2000 mL) and 1N hydrochloric acid (1000 mL) are added at 0-5° C. The mixture is extracted with ethyl acetate (1000 mL). Organic and aqueous layers are separated and the aqueous layer is washed with ethyl acetate (500 mL). The combined organic layers are washed with saturated brine solution (500 mL), dried over sodium sulfate, filtered, and solvent is evaporated to afford a residue that is a mixture of trans-5-chloro-2,3,3a,12b-tetrahydro-2-methyl-1H-dibenz[2,3:6,7]oxepino[4,5-c]pyrrol-1-one and cis-5-chloro-2,3,3a,12b-tetrahydro-2-methyl-1H-dibenz[2,3:6,7]oxepino[4,5-c]pyrrol-1-one. The residue is purified by chromatography on silica. The cis-isomer is eluted with a mixture of 60% ethyl acetate in n-hexane. The fractions containing cis-isomer of the desired purity are combined and concentrated. The solid thus obtained is stirred with n-hexane and dried to afford the title compound. Yield: 12 g. Purity by HPLC: 96.23%.

Example 6

Preparation of trans-5-chloro-2,3,3a,12b-tetrahydro-2-methyl-1H-dibenz[2,3:6,7]oxepino[4,5-c]pyrrol-1-one, or a mixture of cis-5-chloro-2,3,3a,12b-tetrahydro-2-methyl-1H-dibenz[2,3:6,7]oxepino[4,5-c]pyrrol-1-one and trans-5-chloro-2,3,3a,12b-tetrahydro-2-methyl-1H-dibenz[2,3:6,7]oxepino[4,5-c]pyrrol-1-one enriched with trans-5-chloro-2,3,3a,12b-tetrahydro-2-methyl-1H-dibenz[2,3:6,7]oxepino[4,5-c]pyrrol-1-one To a solution of cis-5-chloro-2,3,3a,12b-tetrahydro-2-methyl-1H-dibenz[2,3:6,7]oxepino[4,5-c]pyrrol-1-one (12 g) in toluene (480 mL) is added 1,8-diazabicyclo[5.4.0]undec-7-ene ("DBU," 2.4 g) and the mixture is maintained for 10-15 hours at 25-30° C. Water (240 mL) and acetic acid (4 mL) are added. Organic and aqueous layers are separated and the organic layer is washed with water (200 mL). The solvent is evaporated from the organic layer. The residue is purified by chromatography on silica. Trans-5-chloro-2,3,3a,12b-tetrahydro-2-methyl-1H-dibenz[2,3:6,7]oxepino[4,5-c]pyrrol- 1-one is eluted with a mixture of 25-30% ethyl acetate in n-hexane, and the cis-isomer is eluted with ethyl acetate. The fractions containing trans-isomer of a desired purity are combined and concentrated to afford a crude trans-isomer. As described above, combined fractions containing cis-isomer are reacted with 1,8-diazabicyclo[5.4.0]undec-7-ene (DBU) in toluene and purified by chromatography to afford trans-isomer. This process is again repeated with combined fractions containing cis-isomer. The crude trans-isomer is used for the next reaction step without further purification. Trans-isomer yield: 6.3 g. Recovered cis-isomer: 3.0 g.

Example 7

Preparation of a mixture of cis-5-chloro-2,3,3a,12b-tetrahydro-2-methyl-1h-dibenz[2,3:6,7]oxepino[4,5-c]pyrrol-1-one and trans-5-chloro-2,3,3a,12b-tetrahydro-2-methyl-1H-dibenz[2,3:6,7]oxepino[4,5-c]pyrrol-1-one enriched with trans-5-chloro-2,3,3a,12b-tetrahydro-2-methyl-1H-dibenz[2,3:6,7]oxepino[4,5-c]pyrrol-1-one To a solution of cis-5-chloro-2,3,3a,12b-tetrahydro-2-methyl-1H-dibenz[2,3:6,7]oxepino[4,5-c]pyrrol-1-one (3 g) in toluene (120 mL) is added sodium methoxide (2.4 g) and the mixture is heated at reflux for 5-6 hours. Water (60 mL) and acetic acid (1 mL) are added to the mass. Organic and aqueous layers are separated and the aqueous layer is washed with toluene (30 mL). The combined organic layer is washed with water (60 mL). The solvent is evaporated from the organic layer to afford a residue. Diethyl ether (60 mL) is added to the residue and the mixture is stirred for 15-30 minutes at 25-30° C. Solid is collected by filtration, washed with diethyl ether (30 mL) and dried to afford a crude mixture of trans-5-chloro-2,3,3a,12b-tetrahydro-2-methyl-1H-dibenz[2,3:6,7]oxepino[4,5-c]pyrrol-1-one (29.08%) and cis-5-chloro-2,3,3a,12b-tetrahydro-2-methyl-1H-dibenz[2,3:6,7]oxepino[4,5-c]pyrrol-1-one (63.9%). Yield: 1.0 g.

Ethyl acetate (6 mL) and n-hexane (60 mL) are combined with the crude mixture and stirred for 12-15 hours at 25-30° C. The solid is collected by filtration, washed with n-hexane (20 mL), and dried to afford a mixture of trans-isomer (61.3%) and cis-isomer (33.2%). Yield: 0.35 g.

Example 8

Preparation of trans-5-chloro-2,3,3a,12b-tetrahydro-2-methyl-1H-dibenz[2,3:6,7]oxepino[4,5-c]pyrrol-1-one or a mixture of cis-5-chloro-2,3,3a,12b-tetrahydro-2-methyl-1H-dibenz[2,3:6,7]oxepino[4,5-c]pyrrol-1-one and trans-5-chloro-2,3,3a,12b-tetrahydro-2-methyl-1H-dibenz[2,3:6,7]oxepino[4,5-c]pyrrol-1-one enriched with trans-5-chloro-2,3,3a,12b-tetrahydro-2-methyl-1H-dibenz[2,3:6,7]oxepino[4,5-c]pyrrol-1-one To a solution of cis-5-chloro-2,3,3a,12b-tetrahydro-2-methyl-1H-dibenz[2,3:6,7]oxepino[4,5-c]pyrrol-1-one (27 g) in toluene (1080 mL) is added 1,8-diazabicyclo[5.4.0]undec-7-ene (DBU) (5.1 g) and the mixture is maintained for 15-20 hours at 25-30° C. Water (540 mL) and acetic acid (8.5 mL) are added. Organic and aqueous layers are separated and the organic layer is washed with water (450 mL). The solvent is evaporated from the organic layer. Diethyl ether (270 mL) is added to the residue and maintained for 1-2 hours at 0-5° C. The solid is collected by filtration, washed with diethyl ether (135 mL), and dried to afford the cis-isomer (19.0 g). The filtrate is evaporated to afford a residue.

The residue is dissolved in methanol (20 mL) at room temperature, and then the solution is maintained for 1-2 hours at 0-5° C. Precipitated solid is collected by filtration, washed with methanol (20 mL) and dried to afford a mixture of trans-5-chloro-2,3,3a,12b-tetrahydro-2-methyl-1H-dibenz[2,3:6,7]oxepino[4,5-c]pyrrol-1-one and cis-5-chloro-2,3,3a,12b-tetrahydro-2-methyl-1H-dibenz[2,3:6,7]oxepino[4,5-c]pyrrol-1-one enriched with trans-5-chloro-2,3,3a,12b-tetrahydro-2-methyl-1H-dibenz[2,3:6,7]oxepino[4,5-c]pyrrol-1-one. The recovered cis-isomer (19.0 g) is reacted with 1,8-diazabicyclo[5.4.0]undec-7-ene (DBU) in toluene, as described above, and subsequently the separation as described above is repeated to afford a mixture of trans-5-chloro-2,3,3a,12b-tetrahydro-2-methyl-1H-dibenz[2,3:6,7]oxepino[4,5-c]pyrrol-1-one and cis-5-chloro-2,3,3a,12b-tetrahydro-2-methyl-1H-dibenz[2,3:6,7]oxepino[4,5-c]pyrrol-1-one enriched with trans-5-chloro-2,3,3a,12b-tetrahydro-2-methyl-1H-dibenz[2,3:6,7]oxepino[4,5-c]pyrrol-1-one.

The combined fractions of a mixture of trans-5-chloro-2,3,3a,12b-tetrahydro-2-methyl-1H-dibenz[2,3:6,7]oxepino[4,5-c]pyrrol-1-one and cis-5-chloro-2,3,3a,12b-tetrahydro-2-methyl-1H-dibenz[2,3:6,7]oxepino[4,5-c]pyrrol-1-one enriched with trans-5-chloro-2,3,3a,12b-tetrahydro-2-methyl-1H-dibenz[2,3:6,7]oxepino[4,5-c]pyrrol-1-one are further purified by heating at reflux in methanol (36 mL), precipitating the solid at 0-5° C., filtering the solid, and drying at 40-45° C., to afford trans-5-chloro-2,3,3a,12b-tetrahydro-2-methyl-1H-dibenz[2,3:6,7]oxepino[4,5-c]pyrrol-1-one (95.99%) and cis-5-chloro-2,3,3a,12b-tetrahydro-2-methyl-1H-dibenz[2,3:6,7]oxepino[4,5-c]pyrrol-1-one (1.61%). Yield: 4.8 g. Recovered cis-isomer: 14.0 g.

Example 9

Preparation of Asenapine

Aluminum chloride (4.4 g) is added to tetrahydrofuran (315 mL) at 25-30° C. The solution is cooled and lithium aluminum hydride (2.2 g) is added. A solution of trans-5-chloro-2,3,3a,12b-tetrahydro-2-methyl-1H-dibenz[2,3:6,7]oxepino[4,5-c]pyrrol-1-one in tetrahydrofuran (150 mL) is added in drops at −5 to 5° C. and the mixture is maintained for 15-30 minutes. A 0.6N sodium hydroxide solution (75 mL) is added in drops at −5 to 5° C. The mixture is extracted with ethyl acetate (250 mL) and layers are separated, then the aqueous layer is washed with ethyl acetate (200 mL). The combined organic layer is washed twice with saturated brine solution (2×200 mL). After drying over anhydrous sodium sulfate, the solvent is removed to afford a residue containing asenapine, which is used for the next reaction step without further purification. Yield: 6.3 g. Purity by HPLC: 87.97%.

Example 10

Preparation of Asenapine Maleate

To a solution of maleic acid (3.38 g) in isopropyl alcohol (27 mL) is added a solution of asenapine (6.3 g) in isopropyl alcohol (90 mL) and the mixture is maintained for 15-30 minutes at 60° C. The mass is then cooled to 25-30° C. and seeded with asenapine maleate (50 mg). The mass is maintained for 10-15 hours at 25-30° C., then the mass is slowly allowed to cool to 0-5° C. and stirred for another 1-2 hours. The solid is separated by filtration and washed with cooled isopropyl alcohol (20 mL). The solid is vacuum dried to afford asenapine maleate. Yield: 3.95 g. Purity by HPLC: 97.72%.

Example 11

Preparation of Asenapine Maleate Monoclinic Form

Aluminum chloride (2.7 g) is added to tetrahydrofuran (60 mL) at 25-30° C. The solution is cooled to 0-10° C. and lithium aluminum hydride (1.08 g) is added. The mixture is stirred for 15-30 minutes. A solution of trans-5-chloro-2,3,3a,12b-tetra hydro-2-methyl-1H-dibenz[2,3:6,7]oxepino[4,5-c]pyrrol-1-one (6.0 g) in tetrahydrofuran (120 mL) is added drop-wise at 0-10° C. and the mixture is maintained for 1 hour. Sodium hydroxide solution (0.6N, 100 mL) is added at 0-10° C. The mixture is extracted with ethyl acetate (75 mL) and layers are separated, then the aqueous layer is washed with ethyl acetate (25 mL). The combined organic layer is washed with saturated brine solution (2×100 mL). The organic layer is dried over anhydrous sodium sulfate (10 g) and the solvent from the organic layer is evaporated at 45° C. The obtained residue is dissolved in 1-propanol (20 mL) at 25-30° C. This solution is added to a solution of maleic acid (3.2 g) in 1-propanol (10 mL) at 25-30° C. and stirred for 10 minutes, then seeded with asenapine maleate monoclinic form (120 mg). The mixture is stirred at 25-35° C. for 24 hours and the obtained solid is collected by filtration, washed with 1-propanol (5 mL), and dried under reduced pressure at 65° C., to afford 4.9 g of the title compound. Purity by HPLC: 99.59%; PXRD pattern is shown as FIG. 1; endotherm by DSC: 147° C.; weight loss by TGA: 0.04%; moisture content by Karl Fischer (KF): 0.12%; residual solvents: 1-propanol: 150.3 ppm; ethyl acetate: not detected; tetrahydrofuran: not detected; particle size distribution: d(10)=5.671 µm, d(50)=24.077 µm, d(90)=58.716 µm.

Figure 2:
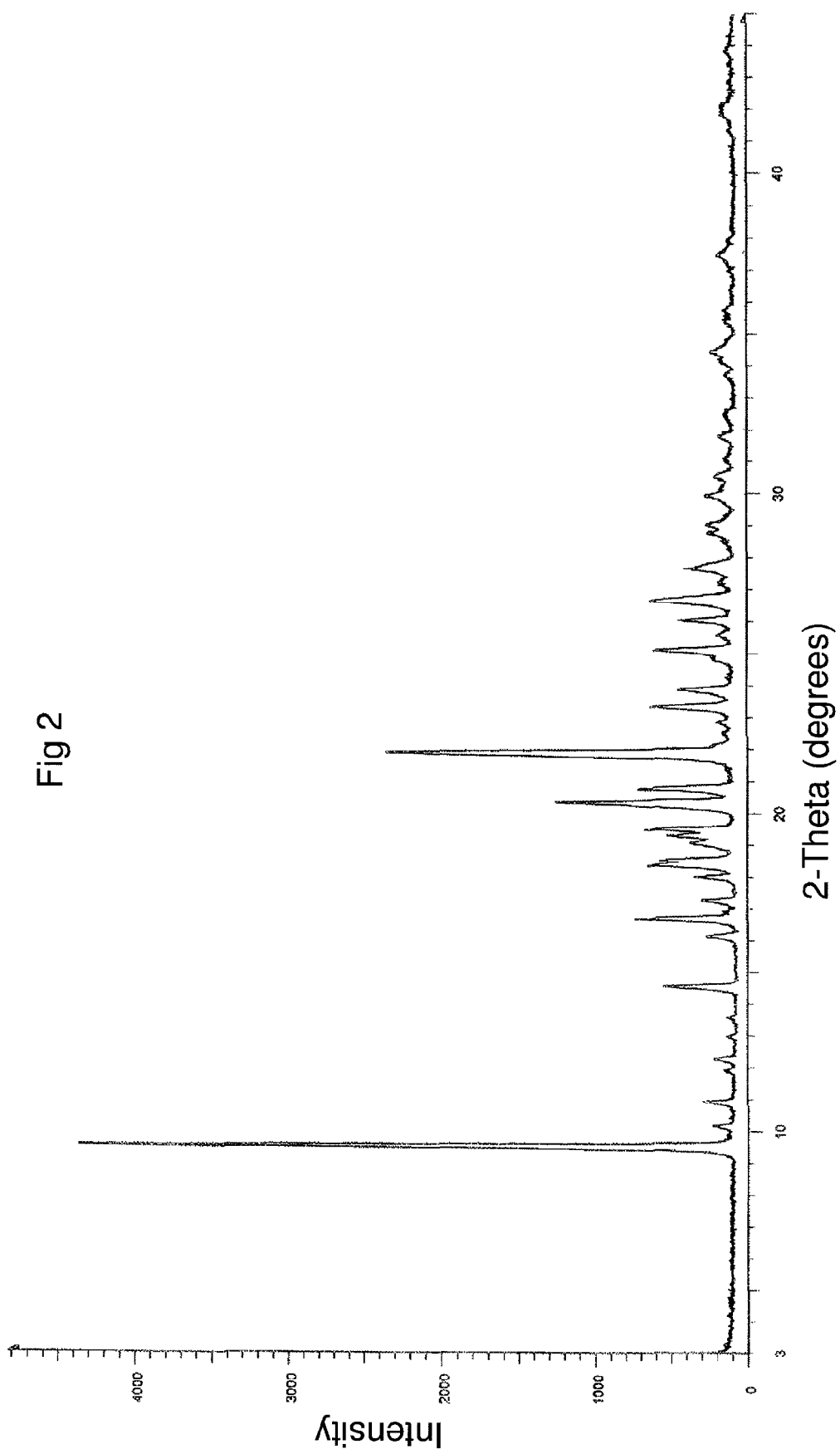
FIG. 2 is an illustration of a PXRD pattern of a microcrystalline monoclinic form of asenapine maleate, prepared in Example 13, after micronization.

A portion of the asenapine maleate monoclinic form is micronized, using a Midas Micronizer 50, manufactured and supplied by Microtek Engineering Company, using nitrogen as the carrier gas with pressures of 4-6 Kg/cm², and the micronized material PXRD pattern is as shown in FIG. 2. Particle size distribution: d(10)=0.994 µm, d(50)=5.516 µm, d(90)=12.715 µm.

Example 12

Preparation of Asenapine Maleate Monoclinic Form

Aluminum chloride (4.40 g) is added to tetrahydrofuran (100 mL) at 25-30° C. The solution is cooled to 0-5° C. and a solution of lithium aluminum hydride (1.80 g) in tetrahydrofuran (19 mL) is added. The mixture is stirred for 15-30 minutes. A solution of trans-5-chloro-2,3,3a,12b-tetrahydro-2-methyl-1H-dibenz[2,3:6,7]oxepino[4,5-c]pyrrol-1-one (10.0 g) in tetrahydrofuran (200 mL) is added by drops at 0-5° C. and the mixture is maintained for 1 hour. Sodium hydroxide solution (0.6N, 120 mL) is added at 0 to 5° C. The mixture is extracted with ethyl acetate (240 mL) and layers are separated, then the aqueous layer is washed with ethyl acetate (80 mL). The combined organic layer is washed with saturated brine solution (2×160 mL). The organic layer is dried over anhydrous sodium sulfate (10 g) and the solvent from the organic layer is evaporated at 45° C. The obtained residue is dissolved in 1-propanol (30 mL) at 25-30° C. This solution is added to a solution of maleic acid (5.3 g) in 1-propanol (20 mL) at 25-30° C. The mixture is stirred at 25-35° C. for 24 hours and the obtained solid is collected by filtration, washed with 1-propanol (5 mL), and dried under reduced pressure at 46° C., to afford 6.2 g of the title compound. PXRD pattern: complies with a reference pattern of monoclinic polymorph.

Example 13

Purification of Asenapine Maleate

Asenapine maleate (34.0 g) and 1-propanol (170 mL) are charged into a round bottom flask and stirred for 5 minutes. The contents are heated to reflux to dissolve asenapine maleate completely. The solution is cooled to 25-35° C., seeded with asenapine maleate monoclinic form (200 mg), and the mixture is stirred at 25-35° C. for 5-6 hours. The obtained solid is collected by filtration, washed with 1-propanol (17 mL), and dried under reduced pressure at 45° C., to afford 23.0 g of the title compound. A portion of the material is micronized, using the procedure described in Example 11. PXRD pattern (before and after micronization): complies with reference pattern of monoclinic polymorph; purity by HPLC: 99.73%; endotherm by DSC: 145° C.; weight loss by TGA: 0.15%; moisture content by KF: 0.20%; residual solvents: 1-propanol: 60.2 ppm, ethyl acetate: not detected, tetrahydrofuran: not detected; particle size distribution (before micronization): d(10)=6.269 µm, d(50)=35.229 µm, d(90)=80.698 µm; particle size distribution (after micronization): d(10)=0.887 µm, d(50)=4.632 µm, d(90)=10.678 µm.

Example 14

Purification of Asenapine Maleate

Asenapine maleate (11.0 g) and 1-propanol (110 mL) are charged into a round bottom flask and stirred for 5 minutes. The mixture is heated to reflux, to dissolve asenapine maleate completely. The solution is cooled to 25-35° C. and stirred for 10-15 minutes. The mixture is further cooled to 0-5° C. and stirred for 1-2 hours. The obtained solid is collected by filtration, washed with 1-propanol (5.5 mL), and dried under reduced pressure at 45° C., to afford 9.9 g of the title compound. PXRD: complies with a reference pattern of the monoclinic polymorph.

Example 15

Preparation of Asenapine Maleate Monoclinic Form

A solution of asenapine (11.0 g) in 2-propanol (50 mL) is added to a solution of maleic acid (4.2 g) in 2-propanol (25 mL) at 25-30° C., then seeded with asenapine maleate monoclinic form (150 mg). The mixture is stirred at 25-35° C. for 14 hours, the obtained solid is collected by filtration, washed with 2-propanol (10 mL), and dried under reduced pressure at 45° C., to afford 8.52 g of the title compound. Particle size distribution: d(10)=4.38 µm, d(50)=14.42 µm, d(90)=33.11 µm.

Example 16

Preparation of Asenapine Maleate Monoclinic Form

Asenapine maleate (5.0 g) and 2-propanol (50 mL) are charged into a round bottom flask and stirred for 5 minutes. The mixture is heated to reflux, to dissolve asenapine maleate completely. The solution is cooled to 25-35° C. and stirred for 15-16 hours. The obtained solid is collected by filtration, washed with 2-propanol (10 mL), and dried under reduced pressure at 45° C., to afford 3.8 g of the title compound. PXRD: complies with reference pattern of the monoclinic polymorph.

Example 17

Micronization of Asenapine Maleate Monoclinic Form

Samples of asenapine maleate monoclinic form prepared according to the process of Example 15 and Example 16 are micronized in a Midas Micronizer 50, using nitrogen as the carrier gas at a pressure of 4-6 Kg/cm$^2$, and results are shown in Table 2.

TABLE 2

| Grams | PXRD Pattern before Micronizing | PXRD Pattern after Micronizing | Particle Size Distribution, μm |
|---|---|---|---|
| 2.0 | Complies with reference monoclinic polymorph | Complies with reference monoclinic polymorph | d(10) = 1.052<br>d(50) = 6.482<br>d(90) = 14.145 |
| 1.0 | Complies with reference monoclinic polymorph | Complies with reference monoclinic polymorph | d(10) = 1.215<br>d(50) = 7.459<br>d(90) = 18.134 |

Micronization of crystals of asenapine maleate having the monoclinic form consistently takes place with retention of the original polymorphic form.

Example 18

Preparation of 2-(2-(4-chlorophenoxy)phenyl)acetic acid xylene (600 mL), potassium carbonate (53.75 g), 4-chlorophenol (46.25 g), and copper powder (2.7 g) are charged in to a round bottom flask at 25-35° C. The reaction mixture heated to 60-70° C., o-chlorophenyl acetic acid (50 g) is added in portions. The reaction mixture is heated to reflux, maintained for 2-3 hours and simultaneously water is removed by azeotropic distillation. The reaction mixture is cooled to below 90° C. Water (600 mL) is added, both layers are separated. The organic layer is washed with water (600 mL). The combined organic layer is cooled to 0-10° C. and conc. HCl (26 mL) is added until the pH reaches to 2.0. The reaction mass is maintained at 0-10° C. for 1 hour, the obtained solid is collected by filtration, washed with water (450 mL), and dried at 60° C. to afford 33.8 g of the title compound.

Example 19

Preparation of ethyl-N-[2-(4-chloro-2-phenoxyphenyl)-1-oxethyl]-N-methylglycinate Ethyl acetate (125 mL) and 2-(2-(4-chlorophenoxy) phenyl)acetic acid (25 g) are charged in to a round bottom flask at 28° C. 1-Hydroxybenzotriazole (13 g) is charged to the reaction mixture at 28° C. and stirred for 10 minutes. Triethylamine (46 mL) is charged to reaction mixture at 28° C. and stirred for 5 minutes. Sarcosine ethyl ester hydrochloride (17.5 g) is added to the reaction mixture at 28° C. and stirred for 30 minutes. The reaction mixture is cooled to 15-20° C. and a solution of dicyclohexylcarbodiimide (DCC; 29.0 g) in ethyl acetate (25 mL) is added to the reaction mixture. The reaction mixture is maintained at 25-35° C. for 2-3 hours. The reaction mixture is cooled to 0° C. and stirred for 30 minutes. The reaction mass is filtered and the solid is washed with ethyl acetate (50 mL). The organic layer is washed with water (250 mL) and 5% sodium bicarbonate solution (200 mL). The organic layer is filtered and washed with water (250 mL). The resultant filtrate is washed with brine solution (250 mL). The solvent from the organic layer is evaporated under reduced pressure at 45° C. to afford 28 g of the title compound.

Example 20

Preparation of 3-(2-(4-chlorophenoxy)phenyl)-1-methylpyrrolidine-2,4-dione

To a suspension of potassium tert-butoxide (148.6 g) in toluene (1800 mL) is added a solution of ethyl-N-[2-(4-chloro-2-phenoxyphenyl)-1-oxethyl]-N-methylglycinate (406 g) in toluene (1800 mL) at 15° C. The resultant reaction mixture maintained at 25-35° C. for 16 hours. Water (1800 mL) is charged to the reaction mixture and stirred for 30 minutes. The organic and aqueous layers are separated. The aqueous layer is washed with ethyl acetate (2500 mL). The aqueous layer is cooled to 0-5° C. and conc. HCl (160 mL) is added until the pH of the aqueous layer reaches 2.0. The reaction mass is maintained at 0-5° C. for 1.5 hour, the obtained solid is collected by filtration, washed with water (1800 mL), and dried at 45° C. The resultant compound (304 g) and toluene (3000 mL) are charged in to a round bottom flask at 25-35° C. The contents are heated to reflux and maintained for 15 minutes. The reaction mass is slowly cooled to 25-35° C. and maintained for 1 hour. The obtained solid is collected by filtration, washed with toluene (600 mL), and dried at 65° C. to afford 256 g of the title compound.

Example 21

Preparation of 5-chloro-2,3-dihydro-2-methyl-1H-dibenz[2,3;6,7]oxepino[4,5-c]pyrrol-1-one Phosphoric acid (270 g) is charged in to a round bottom flask and phosphorous pentoxide (270 g) is added in portions at below 140° C. The reaction mixture temperature is allowed to 110° C. and maintained for 2 hours. 3-(2-(4-Chlorophenoxy)phenyl)-1-methylpyrrolidine-2,4-dione (90 g) is added at 110° C. and maintained for 24 hours. Additional phosphorous pentoxide (3×15 g) is added to the reaction mixture in three portions at 110° C. at the time interval of 24 hours. Finally, the reaction mixture is maintained for 48 hours. The reaction mixture is cooled to 25-35° C., poured in to water (4500 mL), and stirred for 15 hours. The reaction mass is extracted with dichloromethane (900 mL), the layers are separated, and the aqueous layer is washed with dichloromethane (900 mL). The combined organic layer is washed with water (450 mL), 5% sodium bicarbonate (450 mL), and water (450 mL). The solvent from the organic layer is evaporated at 45° C. Methanol (180 mL) is charged to the reaction mass and again the solvent is evaporated form the reaction mass completely at 45° C. under reduced pressure. Methanol (450 mL) is charged to the reaction mass and heated at reflux for 30 minutes. The solution is cooled to 25-35° C. and further cooled to −8 to −12° C. The reaction mass is maintained at −8 to −12° C. for 3 hours, the obtained solid is collected by filtration, washed with chilled methanol (90 mL), and dried at 50-60° C. to afford 44 g of the title compound.

Example 22

Preparation of cis-5-chloro-2,3,3a,12b-tetrahydro-2-methyl-1H-dibenz[2,3:6,7]oxepino[4,5-c]pyrrol-1-one 5-Chloro-2,3-dihydro-2-methyl-1H-dibenz[2,3:6,7]oxepino[4,5-c]pyrrol-1-one (100 g) and methanol (3000 mL) are charged in to a round bottom flask at 25-35° C. Magnesium (8.3 g) is charged to the reaction mixture at 25-35° C. The reaction mixture is heated to reflux temperature and maintained for 20 minutes. The mixture is cooled to 45° C. and then magnesium (8.3 g) is charged. Again the reaction mixture temperature is increased to reflux and maintained for 20 minutes. The reaction mixture is cooled to 45° C. and then magnesium (8.3 g) is charged. Remaining 6 portions of magnesium (each 8.3 g) are charged to the reaction mixture in a similar manner at 40-45° C. and the reaction mixture is maintained at reflux for 15-30 minutes. Water (4500 mL) is added to the reaction mixture. The mixture is cooled to 0-10° C. and conc. HCl (500 mL) is added to the reaction mixture until the pH of the reaction mixture is 1.5. The reaction mass is maintained at 0-10° C. for 1 hour, the obtained solid is collected by filtration, washed with water (1000 mL), and dried at 50-60° C. to afford 96.0 g of the compound. The resultant compound and diethyl ether (1000 mL) are charged in to a round bottom flask. The mixture is heated to reflux and maintained for 10 minutes. The mixture is cooled to 25-35° C., further cooled to 0-5° C., and maintained for 1-2 hours. The obtained solid is collected by filtration, washed with diethyl ether (100 mL), and dried at 50-60° C. to afford 48.5 g of the title compound.

Example 23

Preparation of trans-5-chloro-2,3,3a,12b-tetrahydro-2-methyl-1H-dibenz[2,3:6,7]oxepino[4,5-c]pyrrol-1-one To a solution of cis-5-chloro-2,3,3a,12b-tetrahydro-2-methyl-1H-dibenz[2,3:6,7]oxepino[4,5-c]pyrrol-1-one (100 g) in toluene (4000 mL) is added 1,8-diazabicyclo[5.4.0]undec-7-ene (DBU) (19.3 g) and the mixture is maintained for 4-6 hours at 25-35° C. Water (2000 mL) and acetic acid (32.8 g) are added. Organic and aqueous layers are separated and the organic layer is washed with water (1000 mL). The solvent from the organic layer is evaporated completely at 52° C. under reduced pressure. The reaction mass is cooled to 25-35° C., diethyl ether (1000 mL) is added to the reaction mass, and maintained at the same temperature for 2 hours. The obtained solid is collected by filtration, washed with diethyl ether (200 mL), and dried at 50-60° C. to afford 47 g of cis-isomer. The filtrate is evaporated at 40-50° C. under reduced pressure. Isopropyl alcohol (200 mL) is added to the reaction mass at 25-35° C. and stirred for 5 minutes. The mixture is heated to reflux temperature and maintained for 10-20 minutes. The resultant reaction mass is cooled to 25-35° C., then seeded with trans-5-chloro-2,3,3a,12b-tetrahydro-2-methyl-1H-dibenz[2,3:6,7]oxepino[4,5-c]pyrrol-1-one (0.5 g), and stirred at the same temperature for 15 hours. The obtained solid is collected by filtration, washed with isopropyl alcohol (20 mL), and dried at 50-60° C. to afford 15.0 g of the title compound. Purity by HPLC: 95.9%

Example 24

Purification of trans-5-chloro-2,3,3a,12b-tetrahydro-2-methyl-1H-dibenz[2,3:6,7]oxepino[4,5-c]pyrrol-1-one trans-5-Chloro-2,3,3a,12b-tetrahydro-2-methyl-1H-dibenz[2,3:6,7]oxepino[4,5-c]pyrrol-1-one (20 g) and ethyl acetate (80 mL) are charged in to a round bottom flask and stirred for 5 minutes. The reaction mixture is heated to reflux temperature to dissolve trans-5-chloro-2,3,3a,12b-tetrahydro-2-methyl-1H-dibenz[2,3:6,7]oxepino[4,5-c]pyrrol-1-one completely. Cyclohexane (320 mL) is added to the reaction solution and maintain at reflux for 10 minutes. The reaction mass is cooled to 25-30° C., maintained for 1 hour, then cooled to 10-15° C. and maintained for 1 hour. The obtained solid is collected by filtration, washed with cyclohexane (60 mL), and dried at 60-65° C. to afford 15.9 g of the title compound. Purity by HPLC: 98%

Example 25

Preparation of Asenapine Maleate

Tetrahydrofuran (72 mL) and dichloromethane (8 mL) are charged in to a round bottom flask. The mixture is cooled to −10 to 5° C. and aluminum chloride (4.46 g) is charged in to the mixture. A solution of lithium aluminium hydride in tetrahydrofuran (2.4 M; 19 mL) is added to the reaction mixture at −10° C. to 5° C. A solution of trans-5-chloro-2,3,3a,12b-tetrahydro-2-methyl-1H-dibenz[2,3:6,7]oxepino[4,5-c]pyrrol-1-one (10 g) in a mixture of tetrahydrofuran (108 mL) and dichloromethane (12 mL) is added to the above reaction mixture. The reaction mixture is maintained at −10° C. to 5° C. for 1-2 hours. A 3% sodium hydroxide solution (150 mL) is added to the reaction mixture at below 10° C. and stirred for 30 minutes. Water (150 mL) and ethyl acetate (100 m) are charged in to the mixture. The reaction mass is allowed to warm to 25-35° C., filtered, and the unwanted solid is washed with tetrahydrofuran (50 mL). Separated the organic and aqueous layers, the aqueous layer is extracted with ethyl acetate (80 mL), and the combined organic layer is washed with 30% brine solution (100 mL). The solvent from the organic layer is evaporated completely under reduced pressure at below 50° C. Isopropyl alcohol (2×10 mL) is charged and again the solvent form the mixture is evaporated completely at below 50° C. under reduced pressure. Isopropyl alcohol (50 mL) is charged to the reaction mass. Maleic acid (5.04 g) is added to the reaction mass at 25-35° C. The reaction mixture is stirred at 25-35° C. for 15-30 minutes, then seeded with asenapine maleate (0.1 g) and the mixture is stirred for 15-18 hours at 25-35° C. The reaction mixture is cooled to 0-5° C. and maintained for 1-2 hours. The obtained solid is collected by filtration, washed with isopropyl alcohol (10 mL) at 0-5° C., and dried by suction for 15 minutes to form asenapine maleate. The resultant compound is charged in to another round bottom flask containing a mixture of isopropyl alcohol (40 mL) and methanol (10 mL). The reaction mixture is heated to 60-65° C., basic carbon (1 g) is added to the reaction solution at the same temperature and maintained for 10-20 minutes. The reaction mass is filtered and the solid is washed with isopropyl alcohol (10 mL). The resultant filtrate is charged in to another round bottom flask and maintained at 25-35° C. for 2-3 hours. Then the reaction mass is cooled to 0-5° C. and stirred for 30-60 minutes. The obtained solid is collected by filtration, washed with isopropyl alcohol (10 mL) at 0-5° C., and dried at 60-65° C. under reduced pressure to afford 9.05 g of the title compound. Purity by HPLC: 99.8%; deschloro asenapine of formula (XIII): 0.04%; cis asenapine of formula (XIV): 0.01%; tetrahydro asenapine maleate of formula (XV): not detected; amide compound of formula (XVII): not detected; n-oxide: 0.05%.

Example 26

Purification of Asenapine Maleate

Asenapine maleate (10 g) and 1-propanol (50 mL) are charged in to a round bottom flask and stirred for 5 minutes. The mixture is heated to 65-70° C. and stirred for 15-30 minutes to dissolve asenapine maleate completely. The resultant solution is filtered at 65-70° C. and the solid is washed with 1-propanol (10 mL). The obtained filtrate is transferred in to another round bottom flask and slowly cooled to −5° C. to −10° C. over a period of 140-230 minutes. Seeded with asenapine maleate (100 mg) at 45-50° C. during cooling to −5° C. to −10° C. The reaction mass is maintained for 3 hours at −5 to −10° C. The obtained solid is collected by filtration, washed with 1-propanol (10 mL) at −5 to −10° C., and dried at 65-70° C. under reduced pressure to afford 8.5 g of the title compound. Purity by HPLC: 99.8%; PXRD: complies with reference pattern of the monoclinic polymorph; Particle size distribution d(90)=88 µm; deschloro asenapine of formula (XIII): 0.04%; cis asenapine of formula (XIV): not detected; tetrahydro asenapine maleate of formula (XV): not detected; amide compound of formula (XVII): not detected; n-oxide: 0.02%; 1-propanol content: 611 ppm.

Throughout this application, various publications are referenced. The disclosures of these publications in their entireties are hereby incorporated by reference into this application in order to more fully describe the state of the art as known to those skilled therein as of the date of the application described and claimed herein.

While particular embodiments of the present application have been illustrated and described, it would be obvious to those skilled in the art that various other changes and modifications can be made without departing from the spirit and scope of the application. It is therefore intended to cover in the appended claims all such changes and modifications that are within the scope of this invention.

The invention claimed is:

1. A microcrystalline monoclinic form of asenapine maleate with a powder X-ray diffraction (PXRD) pattern having at least three peaks located at about 9.5, 20.3, 21.9, 23.3, 25.1, 26.1, 26.6, 29.0 or 29.9±0.2 degrees 2-theta.

2. A microcrystalline monoclinic form of asenapine maleate with a powder X-ray diffraction (PXRD) pattern with peaks located substantially as illustrated by FIG. 2.

3. A process for the preparation of the microcrystalline monoclinic form of asenapine maleate of claim 1, comprising:
   (a) providing a solution of asenapine maleate in $C_3$-$C_9$ alcohol or mixtures thereof;
   (b) optionally, seeding the solution prepared in step (a) with crystals of the monoclinic form; and
   (c) isolating the microcrystalline monoclinic form of asenapine maleate.

4. A process for the preparation of the microcrystalline monoclinic form of asenapine maleate of claim 2, comprising:
   (a) providing a solution of asenapine maleate in $C_3$-$C_9$ alcohol or mixtures thereof;
   (b) optionally, seeding the solution prepared in step (a) with crystals of the monoclinic form; and
   (c) isolating the microcrystalline monoclinic form of asenapine maleate.

5. A process for the preparation of the microcrystalline monoclinic form of asenapine maleate of claim 1, comprising:
   (a) providing a solution of asenapine in $C_3$-$C_9$ alcohol or mixtures thereof;
   (b) combining the solution of asenapine obtained in step (a) with a solution of maleic acid in $C_3$-$C_9$ alcohol or mixtures thereof;
   (c) optionally, seeding the solution prepared in step (b) with crystals of the monoclinic form; and
   (d) isolating the microcrystalline monoclinic form of asenapine maleate.

6. A process for the preparation of the microcrystalline monoclinic form of asenapine maleate of claim 2, comprising:
   (a) providing a solution of asenapine in $C_3$-$C_9$ alcohol or mixtures thereof;
   (b) combining the solution of asenapine obtained in step (a) with a solution of maleic acid in $C_3$-$C_9$ alcohol or mixtures thereof;
   (c) optionally, seeding the solution prepared in step (b) with crystals of the monoclinic form; and
   (d) isolating the microcrystalline monoclinic form of asenapine maleate.

7. A process for the preparation of the microcrystalline monoclinic form of asenapine maleate of claim 1, comprising micronizing a monoclinic form of asenapine maleate, wherein said monoclinic form of asenapine maleate has particle size distributions where d(90) is at least 50 µm.

8. A monoclinic form of asenapine maleate, which is stable to micronization, with a powder X-ray diffraction (PXRD) pattern having at least three peaks located at about 9.5, 20.3, 21.9, 23.3, 25.1, 26.1, 26.6, 29.0 or 29.9±0.2 degrees 2-theta.

9. The monoclinic form of asenapine maleate, which is stable to micronization, of claim 8 with a powder X-ray diffraction (PXRD) pattern with peaks located substantially as illustrated by FIG. 1.

10. The monoclinic form of asenapine maleate, which is stable to micronization, of claim 8 with any one or more of a powder X-ray diffraction (PXRD) pattern, a differential scanning calorimetry (DSC) curve, and a thermogravimetric analysis (TGA) curve, substantially as illustrated by FIGS. 1, 3 and 4 respectively.

11. A process for the preparation of the monoclinic form of asenapine maleate, which is stable to micronization, of claim 8, comprising:
   (a) providing a solution of asenapine in $C_3$-$C_9$ alcohol or mixture thereof;
   (b) combining the solution of asenapine prepared in step (a) with a solution of maleic acid in $C_3$-$C_9$ alcohol or mixture thereof;
   (c) optionally, seeding the solution prepared in step (b) with crystals of the monoclinic form; and
   (d) isolating the monoclinic form of asenapine maleate, which is stable to micronization.

12. A process for the preparation of the monoclinic form of asenapine maleate, which is stable to micronization, of claim 8 comprising:
   (a) providing a solution of asenapine maleate in $C_3$-$C_9$ alcohol or mixture thereof;
   (b) optionally, seeding the solution prepared in step (a) with crystals of the monoclinic form; and
   (c) isolating the monoclinic form of asenapine maleate, which is stable to micronization.

13. The process for the preparation of the microcrystalline monoclinic form of asenapine maleate of claim 3, wherein $C_3$-$C_9$ alcohol includes, 2-propanol, 1-propanol, 1-butanol, 2-butanol or mixtures thereof.

14. The process for the preparation of the microcrystalline monoclinic form of asenapine maleate of claim 5, wherein $C_3$-$C_9$ alcohol includes, 2-propanol, 1-propanol, 1-butanol, 2-butanol or mixtures thereof.

15. The process for the preparation of the microcrystalline monoclinic form of asenapine maleate of claim 11, wherein $C_3$-$C_9$ alcohol includes, 2-propanol, 1-propanol, 1-butanol, 2-butanol or mixtures thereof.

16. The process for the preparation of the microcrystalline monoclinic form of asenapine maleate of claim 12, wherein $C_3$-$C_9$ alcohol includes, 2-propanol, 1-propanol, 1-butanol, 2-butanol or mixtures thereof.

17. A pharmaceutical composition comprising microcrystalline monoclinic form of asenapine maleate of claim 1, together with at least one pharmaceutically acceptable excipient.

18. A pharmaceutical composition comprising microcrystalline monoclinic form of asenapine maleate of claim 2, together with at least one pharmaceutically acceptable excipient.

19. A pharmaceutical composition comprising monoclinic form of asenapine maleate, which is stable to micronization, of claim 8, together with at least one pharmaceutically acceptable excipient.

20. A pharmaceutical composition comprising monoclinic form of asenapine maleate, which is stable to micronization, of claim 9, together with at least one pharmaceutically acceptable excipient.

21. A pharmaceutical composition comprising monoclinic form of asenapine maleate, which is stable to micronization, of claim 10, together with at least one pharmaceutically acceptable excipient.

\* \* \* \* \*